United States Patent
Felix et al.

(10) Patent No.: US 9,408,649 B2
(45) Date of Patent: Aug. 9, 2016

(54) RADIOLUCENT SCREW WITH RADIOPAQUE MARKER

(75) Inventors: Brent A. Felix, Sandy, UT (US); David N. McKean, Bountiful, UT (US); David A. Hershgold, Draper, UT (US)

(73) Assignee: Innovasis, Inc., Salt Lake City, UT (US)

( * ) Notice: Subject to any disclaimer, the term of this patent is extended or adjusted under 35 U.S.C. 154(b) by 1067 days.

(21) Appl. No.: 12/208,986

(22) Filed: Sep. 11, 2008

(65) Prior Publication Data

US 2010/0063550 A1 Mar. 11, 2010

(51) Int. Cl.
*A61B 17/86* (2006.01)
*A61B 17/70* (2006.01)
*A61B 19/00* (2006.01)

(52) U.S. Cl.
CPC ......... *A61B 17/8685* (2013.01); *A61B 17/7032* (2013.01); *A61B 17/7037* (2013.01); *A61B 17/866* (2013.01); *A61B 17/864* (2013.01); *A61B 17/8625* (2013.01); *A61B 19/54* (2013.01)

(58) Field of Classification Search
CPC ............. A61B 17/8625; A61B 17/864; A61B 17/866; A61B 17/86; A61B 17/8685
USPC .............. 72/46, 135, 137, 371; 264/250, 257, 264/258, 271.1, 279.1; 470/8, 9, 10, 11, 12; 411/82.2, 901, 902, 903; 623/1.22, 623/16.11
See application file for complete search history.

(56) References Cited

U.S. PATENT DOCUMENTS

| | | | |
|---|---|---|---|
| 1,828,287 A * | 10/1931 | MacBean | 470/11 |
| 2,405,909 A * | 8/1946 | Smith et al. | 156/171 |
| 3,455,360 A * | 7/1969 | Simons | 411/301 |
| 4,063,838 A * | 12/1977 | Michael | 403/343 |
| 4,265,981 A * | 5/1981 | Campbell | 428/591 |
| 4,307,979 A * | 12/1981 | Killmeyer | 405/259.1 |
| 4,329,743 A | 5/1982 | Alexander et al. | |
| 4,403,606 A | 9/1983 | Woo et al. | |
| 4,512,038 A | 4/1985 | Alexander et al. | |
| 4,623,290 A * | 11/1986 | Kikuzawa et al. | 411/350 |
| 4,778,637 A * | 10/1988 | Adams et al. | 264/136 |
| 4,863,330 A * | 9/1989 | Olez et al. | 411/424 |
| 4,863,470 A | 9/1989 | Carter | |
| 5,084,051 A * | 1/1992 | Tormala et al. | 606/77 |

(Continued)

FOREIGN PATENT DOCUMENTS

DE 44 43 051 A1 10/1996
DE 100 65 799 C1 4/2002

(Continued)

OTHER PUBLICATIONS

International Search and Written Opinion issued Feb. 19, 2010, PCT/US2009/056508, filed Sep. 10, 2009.

(Continued)

*Primary Examiner* — Edward Tolan
(74) *Attorney, Agent, or Firm* — Workman Nydegger

(57) ABSTRACT

A bone screw includes an elongate shaft extending longitudinally between a proximal end and an opposing distal end, the shaft bounding a first passageway at least partially extending between the proximal end and the distal end, the shaft being comprised of a radiolucent material. A core is disposed within the first passageway of the shaft, the core being comprised of a radiopaque material. A rounded head or a substantially U-shaped collar is either integrally formed with or is rigidly attached to the proximal end of the shaft.

13 Claims, 18 Drawing Sheets

(56) References Cited

U.S. PATENT DOCUMENTS

| | | | |
|---|---|---|---|
| 5,127,783 A * | 7/1992 | Moghe et al. | 411/411 |
| 5,209,888 A * | 5/1993 | Shimada et al. | 264/250 |
| 5,246,655 A * | 9/1993 | Mitchell et al. | 264/138 |
| 5,366,773 A * | 11/1994 | Schroll et al. | 428/36.9 |
| 5,466,237 A | 11/1995 | Byrd, III et al. | |
| 5,474,555 A | 12/1995 | Puno et al. | |
| 5,540,870 A * | 7/1996 | Quigley | 264/103 |
| 5,676,146 A | 10/1997 | Scarborough | |
| 5,807,051 A | 9/1998 | Heminger | |
| 5,951,556 A * | 9/1999 | Faccioli et al. | 606/65 |
| 6,059,769 A * | 5/2000 | Lunn et al. | 604/523 |
| 6,063,090 A | 5/2000 | Schlapfer | |
| 6,099,528 A | 8/2000 | Saurat | |
| 6,113,826 A * | 9/2000 | Tajima et al. | 264/159 |
| 6,117,173 A | 9/2000 | Taddia et al. | |
| 6,174,329 B1 * | 1/2001 | Callol et al. | 623/1.34 |
| 6,203,568 B1 | 3/2001 | Lombardi et al. | |
| 6,214,921 B1 * | 4/2001 | Bluett et al. | 524/495 |
| 6,248,105 B1 | 6/2001 | Schlapfer et al. | |
| 6,280,442 B1 | 8/2001 | Barker et al. | |
| 6,302,630 B1 | 10/2001 | Grant | |
| 6,340,367 B1 | 1/2002 | Stinson et al. | |
| 6,342,055 B1 | 1/2002 | Eisemann et al. | |
| 6,371,957 B1 | 4/2002 | Amrein et al. | |
| 6,423,067 B1 | 7/2002 | Eisermann | |
| 6,471,705 B1 | 10/2002 | Biedermann et al. | |
| 6,565,567 B1 | 5/2003 | Haider | |
| 6,575,975 B2 | 6/2003 | Brace et al. | |
| 6,599,290 B2 | 7/2003 | Bailey et al. | |
| 6,641,586 B2 | 11/2003 | Varieur | |
| 6,660,004 B2 | 12/2003 | Barker et al. | |
| 6,679,883 B2 | 1/2004 | Hawkes et al. | |
| 6,712,852 B1 | 3/2004 | Chung et al. | |
| 6,740,086 B2 | 5/2004 | Richelsoph | |
| 6,837,905 B1 | 1/2005 | Lieberman | |
| 6,955,513 B2 * | 10/2005 | Niku | 411/382 |
| 6,974,480 B2 | 12/2005 | Messerli et al. | |
| 7,150,594 B2 * | 12/2006 | Keener | 411/34 |
| 7,169,150 B2 | 1/2007 | Shipp et al. | |
| 7,192,447 B2 | 3/2007 | Rhoda | |
| 7,235,079 B2 | 6/2007 | Jensen et al. | |
| 7,235,290 B2 * | 6/2007 | Vallittu et al. | 428/296.7 |
| 7,273,481 B2 | 9/2007 | Lombardo et al. | |
| 7,318,825 B2 | 1/2008 | Butler et al. | |
| 7,524,190 B2 * | 4/2009 | Levin | 434/83 |
| 7,766,942 B2 | 8/2010 | Patterson et al. | |
| 7,966,711 B2 * | 6/2011 | Keener | 29/525.04 |
| 7,988,710 B2 | 8/2011 | Jahjng et al. | |
| 7,998,180 B2 * | 8/2011 | Erickson et al. | 606/286 |
| 8,267,978 B2 | 9/2012 | Lindemann et al. | |
| 8,475,505 B2 * | 7/2013 | Nebosky et al. | 606/304 |
| 2002/0123751 A1 | 9/2002 | Fallin | |
| 2002/0133158 A1 | 9/2002 | Saint Martin | |
| 2003/0078583 A1 | 4/2003 | Biedemann et al. | |
| 2004/0034430 A1 | 2/2004 | Faiahee | |
| 2004/0127904 A1 | 7/2004 | Konieczynski et al. | |
| 2004/0143265 A1 | 7/2004 | Landry et al. | |
| 2004/0199251 A1 | 10/2004 | McCombe et al. | |
| 2004/0210226 A1 | 10/2004 | Trieu | |
| 2004/0210316 A1 | 10/2004 | King et al. | |
| 2004/0215195 A1 | 10/2004 | Shipp et al. | |
| 2004/0243129 A1 | 12/2004 | Moumene et al. | |
| 2005/0187550 A1 | 8/2005 | Grusin | |
| 2005/0187555 A1 | 8/2005 | Biedermann et al. | |
| 2005/0203516 A1 | 9/2005 | Biedermann et al. | |
| 2005/0203517 A1 | 9/2005 | Jahng et al. | |
| 2005/0203519 A1 | 9/2005 | Harms et al. | |
| 2005/0216081 A1 | 9/2005 | Taylor | |
| 2005/0228388 A1 | 10/2005 | Brodke et al. | |
| 2005/0228479 A1 | 10/2005 | Pavcnik et al. | |
| 2006/0041259 A1 | 2/2006 | Paul et al. | |
| 2006/0084986 A1 | 4/2006 | Grinberg et al. | |
| 2006/0085072 A1 | 4/2006 | Funk et al. | |
| 2006/0089644 A1 | 4/2006 | Felix | |
| 2006/0142758 A1 | 6/2006 | Petit | |
| 2006/0149228 A1 | 7/2006 | Schlapfer et al. | |
| 2006/0195093 A1 | 8/2006 | Jahng | |
| 2006/0200140 A1 | 9/2006 | Lange | |
| 2006/0235410 A1 | 10/2006 | Ralph et al. | |
| 2006/0247638 A1 | 11/2006 | Trieu et al. | |
| 2006/0276788 A1 | 12/2006 | Berry et al. | |
| 2007/0123879 A1 | 5/2007 | Songer et al. | |
| 2007/0156145 A1 | 7/2007 | Demakas et al. | |
| 2007/0190230 A1 | 8/2007 | Trieu et al. | |
| 2007/0233071 A1 | 10/2007 | Dewey et al. | |
| 2007/0233073 A1 | 10/2007 | Wisnewski et al. | |
| 2007/0250167 A1 | 10/2007 | Bray et al. | |
| 2007/0270851 A1 | 11/2007 | Erickson et al. | |
| 2008/0033437 A1 | 2/2008 | Shipp et al. | |
| 2008/0065070 A1 | 3/2008 | Freid et al. | |
| 2008/0077133 A1 | 3/2008 | Schulze et al. | |
| 2008/0082103 A1 | 4/2008 | Hutton et al. | |
| 2008/0083613 A1 | 4/2008 | Oi et al. | |
| 2008/0086127 A1 | 4/2008 | Patterson et al. | |
| 2008/0086129 A1 | 4/2008 | Lindemann et al. | |
| 2008/0091214 A1 | 4/2008 | Richelsoph | |
| 2008/0097432 A1 | 4/2008 | Schulze | |
| 2008/0125777 A1 | 5/2008 | Veldman et al. | |
| 2008/0154306 A1 | 6/2008 | Heinz | |
| 2008/0154367 A1 | 6/2008 | Justis et al. | |
| 2008/0243185 A1 | 10/2008 | Felix et al. | |
| 2009/0082810 A1 | 3/2009 | Bhatnagar et al. | |
| 2009/0093819 A1 | 4/2009 | Joshi | |
| 2009/0093844 A1 | 4/2009 | Jackson | |
| 2009/0112265 A1 | 4/2009 | Hudgins et al. | |
| 2009/0240284 A1 | 9/2009 | Randol et al. | |
| 2009/0275983 A1 | 11/2009 | Veldman et al. | |
| 2009/0326582 A1 | 12/2009 | Songer et al. | |
| 2010/0042215 A1 * | 2/2010 | Stalcup et al. | 623/16.11 |
| 2010/0063550 A1 | 3/2010 | Felix | |
| 2010/0114167 A1 | 5/2010 | Wilcox et al. | |
| 2010/0160967 A1 | 6/2010 | Capozzoli | |
| 2012/0109207 A1 | 5/2012 | Trieu | |

FOREIGN PATENT DOCUMENTS

| | | |
|---|---|---|
| FR | 2 899 787 | 10/2007 |
| GB | 2 294 399 | 1/1996 |
| JP | 2005-270250 | 10/2005 |
| JP | 2006-187658 | 7/2006 |
| JP | 2007-307368 | 11/2007 |
| WO | WO 94/04095 A1 | 3/1994 |
| WO | WO 2007/127845 | 11/2007 |

OTHER PUBLICATIONS

Office Action dated Nov. 9, 2011, issued in U.S. Appl. No. 12/557,081, filed Sep. 10, 2009.

Office Action dated Jan. 19, 2012, issued in U.S. Appl. No. 12/719,765, filed Mar. 8, 2010.

PCT/US2011/024935, May 23, 2011, International Search Report and Written Opinion.

PCT/US2010/048243, Nov. 10, 2010, International Search Report and Written Opinion.

*VLS System Variable Locking Screw*, Interpore Cross International, 2001.

EBI Spine Systems, *EBI Ωmega21 Spinal Fixation System, Surgical Technique*, published at least as early as Sep. 1, 2006.

*Click'X Top Loading System, Technique Guide*, Synthes Spine 2003.

*Synergy IQ, Low Back Surgical Technique*, Interpore Cross International, 2003.

S. Kawahara et al., Summary of *Clinical Imaging Diagnosis of Implant Materials for Breast Augmentation*, Ann Plast Surg., Jul. 2006; 57(1), pp. 6-12 (1 page).

Office Action dated May 3, 2013, issued in U.S. Appl. No. 13/063,605, filed Mar. 11, 2011.

Final Office Action dated Jun. 6, 2012, issued in U.S. Appl. No. 12/577,081, filed Sep. 10, 2009.

Final Office Action dated May 9, 2012, issued in U.S. Appl. No. 12/719,765, filed Mar. 8, 2010.

Office Action dated Aug. 17, 2012, issued in U.S. Appl. No. 12/719,765, filed Mar. 8, 2010.

(56) References Cited

OTHER PUBLICATIONS

Office Action issued dated Feb. 16, 2013, issued in Chinese Application No. 200980144925.0, filed Sep. 11, 2011.
Office Action dated Sep. 14, 2011 issued in EP Application No. 09792417.9, filed Sep. 11, 2011.
Final Office Action dated Apr. 13, 2013 issued in U.S. Appl. No. 12/719,765, filed Mar. 8, 2010.
Office Action dated Apr. 11, 2013, issued in U.S. Appl. No. 12/719,765, filed Mar. 8, 2010.
Office Action dated May 3, 2013, issued in U.S. Appl. No. 13/063,605, Mar. 11, 2011.
Office action dated Jul. 30, 2013, issued in MX/a/2011/002706, filed Mar. 11, 2011.
Office Action dated Oct. 15, 2013, issued in JP 2011-526971, filed May 16, 2011.
Office Action dated Feb. 16, 2013, issued in CN200980144925.0.
Office Action dated Nov. 18, 2013, issued in U.S. Appl. No. 12/719,765, filed Mar. 8, 2010.
Office Action dated Jan. 16, 2014, issued in U.S. Appl. No. 13/063,605, filed Mar. 11, 2011.
Office Action dated Nov. 6, 2013, issued in CN200980144925.0.
Office Action dated Aug. 15, 2013, issued in U.S. Appl. No. 12/557,081, filed Sep. 10, 2009.
Office Action dated Jan. 2, 2014, issued in U.S. Appl. No. 12/557,081, filed Sep. 10, 2009.
Office Action dated Feb. 20, 2014, issued in U.S. Appl. No. 12/557,081, filed Sep. 10, 2009.
Office Action dated Apr. 23, 2014, issued in U.S. Appl. No. 13/063,605, filed Mar. 11, 2011.

* cited by examiner

RADIOLUCENT SCREW WITH RADIOPAQUE MARKER

CROSS-REFERENCE TO RELATED APPLICATIONS

Not Applicable.

BACKGROUND OF THE INVENTION

1. The Field of the Invention

The present invention relates to polyaxial and fixed bone screws and components thereof that can be used for stabilizing adjacent vertebrae of the spine or other adjacent bones.

2. The Relevant Technology

Polyaxial screws are commonly used in spinal operations for adjusting or stabilizing adjacent vertebrae. For example, in one conventional procedure a first polyaxial screw is screwed into a first vertebra while a second polyaxial screw is screwed into an adjacent second vertebra. A stabilizing rod is then secured between the polyaxial screws so as to fix the adjacent vertebrae relative to each other. Polyaxial screws can be positioned on each side of each vertebra and can be positioned in any number of consecutive vertebrae with one or more rods extending between the different polyaxial screws.

A conventional polyaxial screw comprises a bone screw having a collar pivotably mounted on the end thereof. The bone screw is inserted into the bone and the stabilizing rod is received within the collar and secured therein. To be strong enough to handle the stresses placed upon it, the polyaxial screw is made of titanium or some other biocompatible metal. Being made of metal allows the doctor to view the bone screw using X-ray photographs during and after implantation.

However, because the bone screws are made of metal, the screws block X-rays passing through the body, in effect obscuring adjacent bone and other X-ray viewable internal structures surrounding the area and thereby preventing the surgeon from viewing those structures on an X-ray photograph. This can limit a surgeon's ability to ensure proper placement of the bone screw and diagnose and treat problems that arise near the location of the bone screw after the bone screw has been implanted.

Accordingly, what is needed are polyaxial and fixed bone screws that overcome some or all of the above disadvantages.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
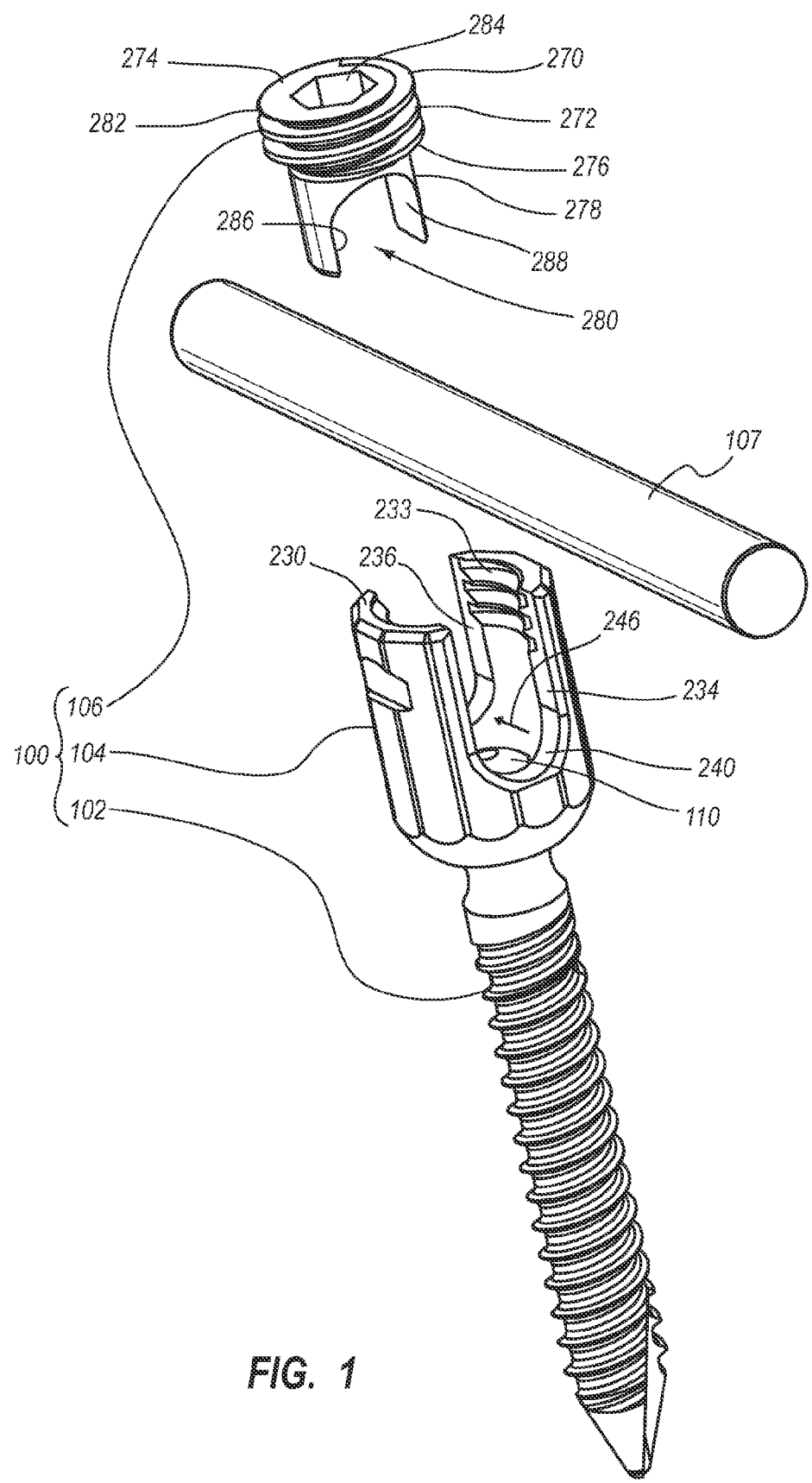
FIG. 1 is a perspective view of one embodiment of a polyaxial screw of the present invention.

Depicted in FIG. 1 is one embodiment of a polyaxial screw 100 incorporating features of the present invention. In one embodiment polyaxial screw 100 can be used for stabilizing adjacent vertebrae of a spine as part of a procedure for fusing together the adjacent vertebrae. Polyaxial screw 100 can also be used for stabilizing a series of consecutive vertebrae for manipulation of the spine to correct spinal deformities such as scoliosis. It is appreciated that polyaxial screw 100 and/or discrete elements thereof can also be used in other procedures for anchoring, manipulating, and/or stabilizing portions of the spine or other bones.

As depicted in FIG. 1, polyaxial screw 100 comprises an elongated bone screw 102, a collar 104 pivotally mounted on bone screw 102, and a fastener 106 selectively engageable with collar 104 to secure polyaxial screw 100 to a stabilizing rod 107. The above identified components of polyaxial screw 100 and their relative interaction will now be discussed in greater detail.

Figure 2:
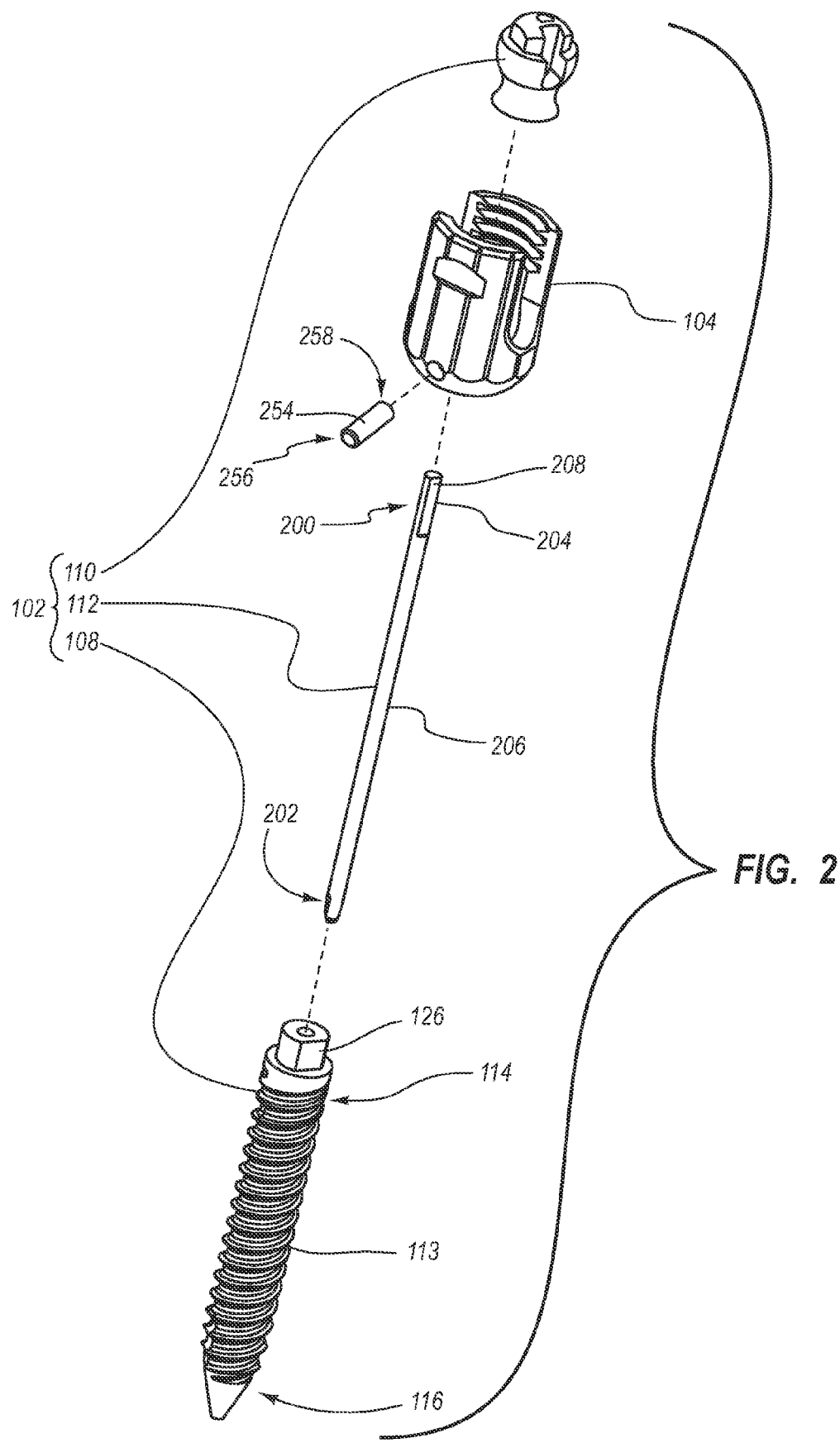
FIG. 2 is an exploded perspective view of a portion of the polyaxial screw shown in FIG. 1.
Figure 3:
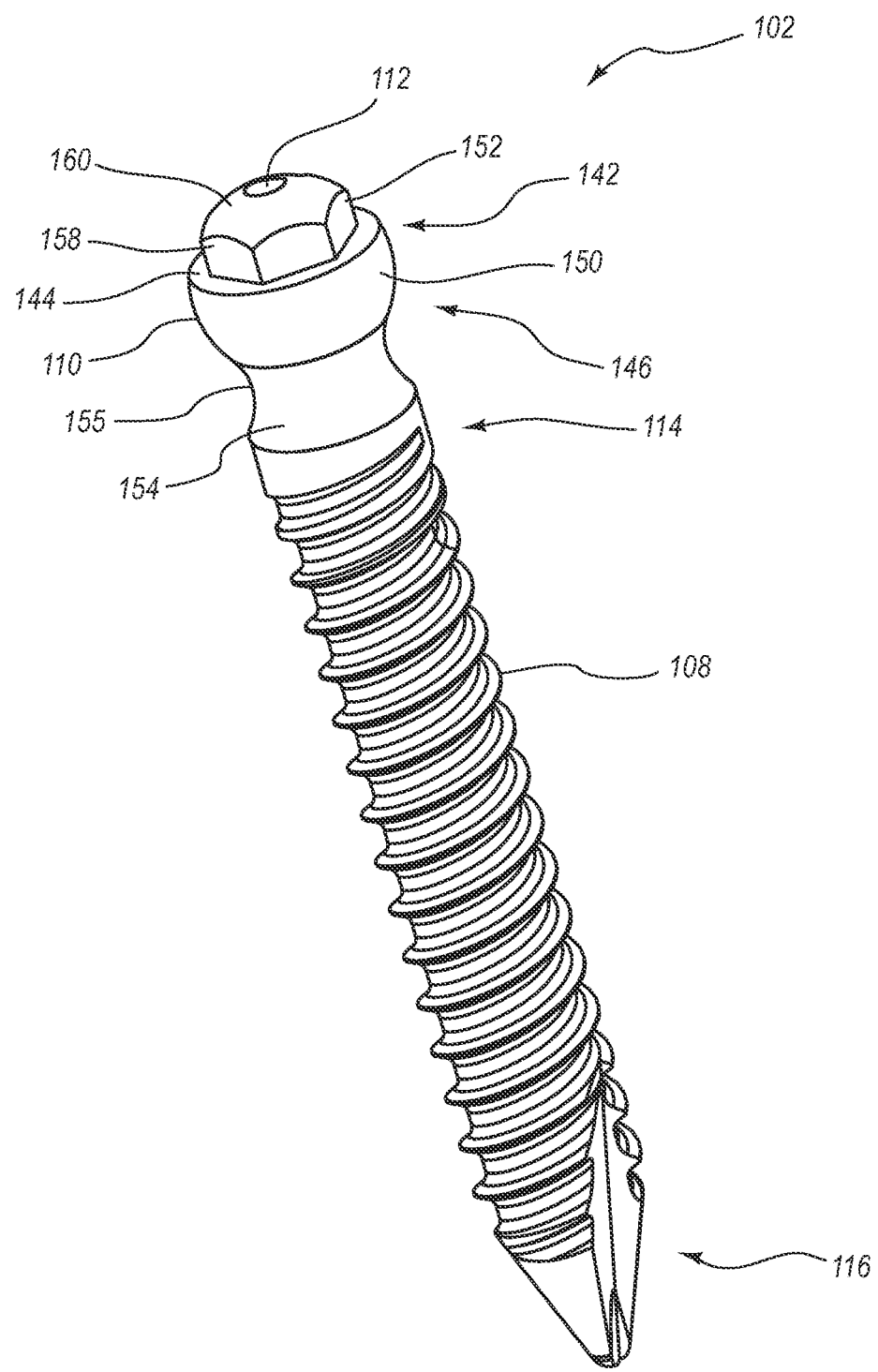
FIG. 3 is a perspective view of the assembled bone screw shown in FIG. 2.

As shown in FIGS. 2 and 3, bone screw 102 comprises an elongated shaft 108 having a head 110 disposed thereon with a core 112 extending longitudinally through shaft 108 and head 110.

Figure 4:
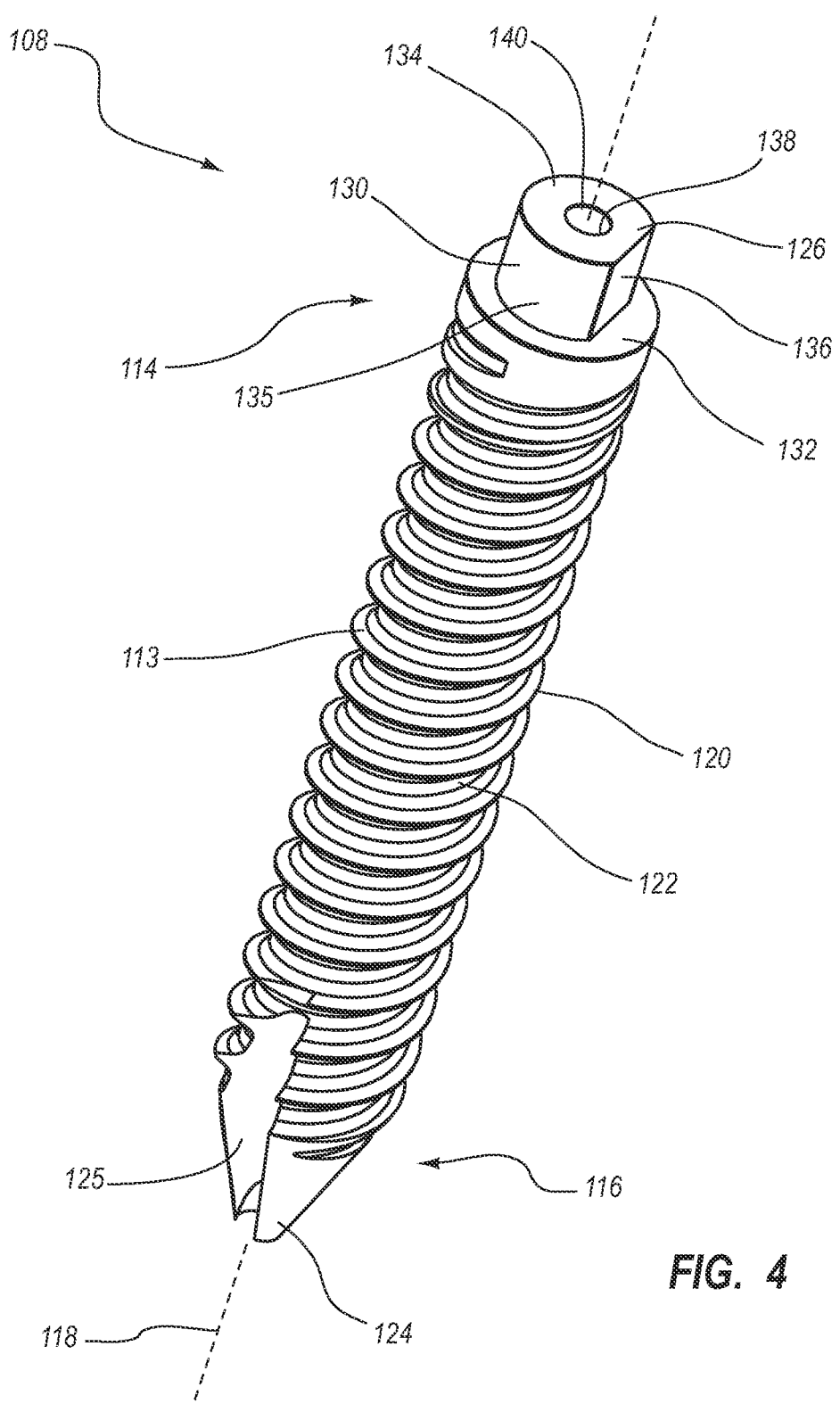
FIG. 4 is a perspective view of the shaft portion of the bone screw shown in FIG. 2.

Turning to FIG. 4, shaft 108 is elongated and has a proximal end 114 and a spaced apart distal end 116 with a central longitudinal axis 118 extending therebetween. Shaft 108 comprises an elongated shaft body 113 and an attachment member 126 formed thereon. Shaft body 113 has an exterior surface 122 that extends between proximal end 114 and distal end 116. One or more threads 120 helically encircle and radially outwardly project from exterior surface 122 of shaft 108 along the length thereof. The one or more threads 120 can have a variety of different pitches and configurations, and, if desired, can be self tapping. Proximal end 114 of shaft body 113 terminates at an end face 132 while distal end 116 of shaft body 113 terminates at a tapered tip 124. End face 132 is typically planar and disposed orthogonal to central longitudinal axis 118, although this is not required. Tapered tip 124 has a substantially conical configuration for ease in penetration into a bone or predrilled hole. A cutting edge 125 can also be disposed on the tapered portion of tip 124 to aid in cutting the bone in bone screw embodiments that are self tapping.

Attachment member 126 centrally projects from end face 132 of shaft body 113. As discussed below in greater detail, attachment member 126 is used to engage and secure head 110 to shaft 108. As such, attachment member 126 is sized and shaped so as to fit within a complementary attachment recess 128 disposed on head 110 (see FIG. 6). In the embodiment depicted, attachment member 126 has an encircling side wall 130 that proximally extends from end face 132 of shaft body 113 to a terminal end face 134. End faces 132 and 134 are depicted as being substantially parallel with each other and orthogonal to longitudinal axis 118, although this is not required. Side wall 130 is depicted as being substantially parallel to longitudinal axis 118, but this is also not required.

In the depicted embodiment, side wall 130 of attachment member 126 comprises a substantially cylindrical portion 135 and a flat 136. Flat 136 in effect removes a portion of the rounded side of the cylinder portion 135. In an alternative embodiment side wall 130 is formed without a flat. Other cross sectional attachment shapes can alternatively be used. For example, side wall 130 of attachment member 126 can be oval, polygonal, star shaped, irregular, or the like. Other shapes are also possible.

Continuing with FIG. 4, shaft 108 includes an internal surface 138 that bounds a first passageway 140 that extends longitudinally through shaft 108 between proximal end 114 and distal end 116. First passageway 140 extends along central longitudinal axis 118, through terminal end face 134 of attachment member 126 and through tapered tip 124. In the embodiment depicted, first passageway 140 has a substantially circular cross-sectional shape. Other shapes can alternatively be used. For example, first passageway 140 can be oval shaped, star shaped, polygonal shaped, or the like. First passageway 140 can also be symmetrically or non-symmetrically shaped.

Shaft 108 can be comprised of a radiolucent material that will allow viewing of adjacent bone or other internal structures on an X-ray photograph that are in the viewing path of shaft 108. Using radiolucent material for the shaft 108 will also minimize scattering caused by commonly used metallic or other radiopaque shafts in X-Rays, CAT scans, MRI's, and other types of imaging systems. One example of a radiolucent material that can be used in shaft 108 is a biocompatible fiber and adhesive matrix, such as a carbon fiber epoxy matrix. In such a matrix, biocompatible fibers are impregnated with an epoxy resin, molten plastic, or other type of adhesive, then wound about a rod or other object to create many layers wound on top of each other. The fibers can be wound one fiber at a time or multiple fibers at a time in a fiber bundle or tow. Alternatively, the fibers can be included in a sheet and the sheet wound about the rod. Various winding patterns can also be used. Many types of biocompatible fibers and adhesives can be used. Methods of manufacturing the shaft 108 and other portions of the bone screw 102 are discussed in more detail below.

In one embodiment, the fibers comprise a continuous high strength, PAN based carbon fiber, 34-700, 12 k (tow), "unsized" and approved for permanent implant. By "unsized," it is meant that the fibers have not been coated with a material to improve adhesion of the resin or adhesive. Other types or sizes of biocompatible fibers can also be used, such as fiberglass, kevlar or other biocompatible fibers.

Examples of biocompatible epoxies that can be used to bond the fibers include the Master Bond Inc. epoxies EP42HT-2 and EP45HT MED and the Epotek epoxies 301-2 and 375. Other epoxies that are implantable, biocompatible, sterilizable, and have the desired strength properties can also be used. Examples of biocompatible resins that can be used to bond the fibers include polyetheretherketone (PEEK), polyethylene, polyurethane, polyimide, and polyamide. Other materials can alternatively be used.

Figure 15:
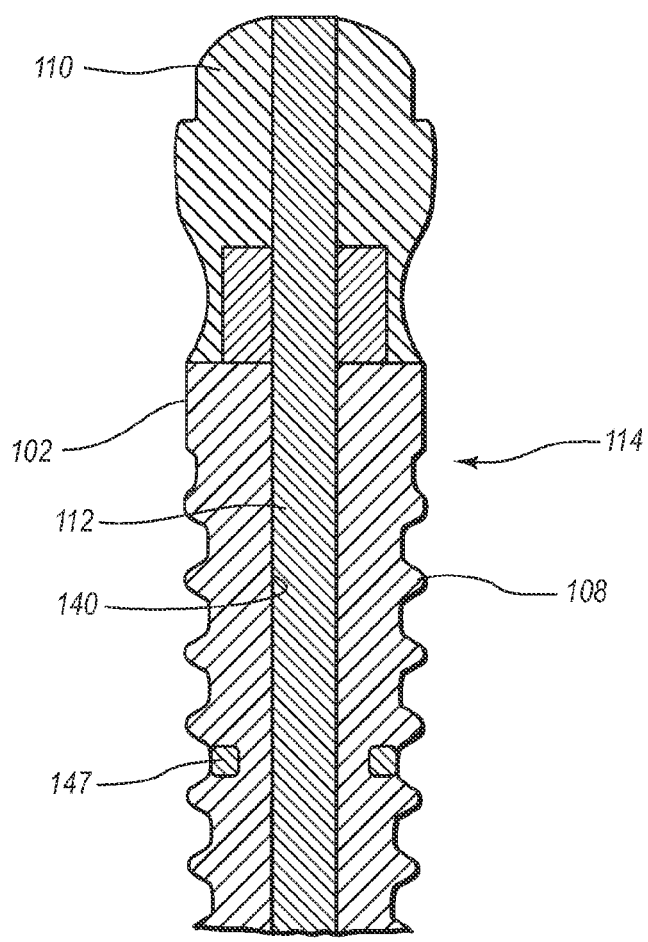
FIG. 15 is a cross sectional side view of a portion of an assembled bone screw according to one embodiment.

To aid in implantation of the bone screw, an encircling marker can be included within shaft 108 that is spaced apart from first passageway 140. For example, as shown in FIG. 15, in one embodiment a biocompatible positioning ring 147 is embedded within shaft 108 between proximal end 114 and distal end 116. In the depicted embodiment, positioning ring 147 is substantially orthogonal to and substantially encircles first passageway 140. Other configurations are also possible. Positioning ring 147 is comprised of a radiopaque material, such as titanium, stainless steel, an alloy or the like so as to be viewable on an X-Ray photograph. During implantation of bone screw 102, the X-Ray image of positioning ring 147 can help the physician determine the position and orientation of bone screw 102, as described in detail below.

Figure 16:
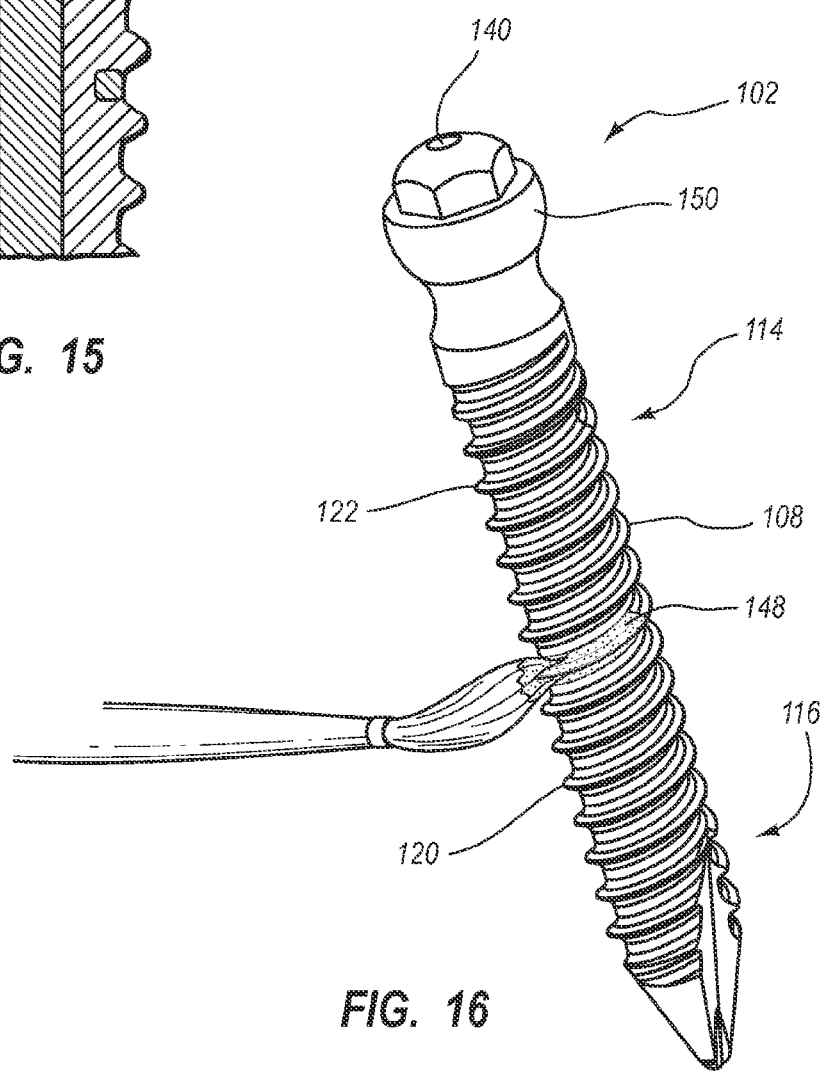
FIG. 16 is a perspective view of an assembled bone screw according to one embodiment having a ring layer painted thereon.

In another embodiment, a thin ring layer can be affixed or otherwise placed on exterior surface 122 in place of or in addition to ring 147. For example, as shown in FIG. 16, thin ring layer 148 is disposed on exterior surface 122 within threads 120 between proximal end 114 and distal end 116 of shaft 108 so as to substantially encircle first passageway 140. In one embodiment, ring layer 148 comprises a radiopaque material that is painted onto threads 120, as in the depicted embodiment. In the depicted embodiment, ring layer 148 is painted on a single helical revolution of threads 120, although more revolutions, complete or partial, can also be used. Similar to positioning ring 147, ring layer 148 is comprised of a radiopaque material, such as titanium, stainless steel, an alloy or the like so as to be viewable on an X-Ray photograph.

In one embodiment, positioning ring 147 and/or ring layer 148 are positioned about midway between proximal end 114 and distal end 116. In other embodiments, positioning ring 147 and/or ring layer 148 are positioned substantially closer to proximal end 114 and in still other embodiments substantially closer to distal end 116. In other embodiments it is appreciated that two or more positioning rings 147 and/or ring layers 148 can be positioned along shaft 108 at spaced apart locations. Furthermore, in alternative embodiments the marker need not be a ring but can be any desired shape and at any position or orientation that will produce a desired marking.

Returning to FIGS. 2 and 3, head 110 is disposed on proximal end 114 of shaft 108 so as to engage with attachment member 126. As shown in FIG. 3, head 110 comprises a rounded substantially semi-spherical bottom portion 150 that can bias and rotate against collar 104. Bottom portion 150 has a first end 142 on which a face 144 is formed and a second end 146. A top portion 152 centrally projects from face 144 and is shaped to allow a tool to engage and rotate bone screw 102. An annular neck 154 extends from the second end 146 of bottom portion 150 of head 110 to a bottom surface 156 (see FIG. 6). Neck 154 has an encircling exterior surface 155 having a substantially concave configuration. In the depicted embodiment, top portion 152 has an encircling sidewall 158 that extends from face 144 to a top surface 160. Top portion 152 has a polygonal shape so that it can mate with a driver or other tool for tightening and loosening bone screws. Other shapes can also be used. Alternatively, a socket can be formed within top surface 160 or on face 144 of bottom portion 150.

Figure 5:
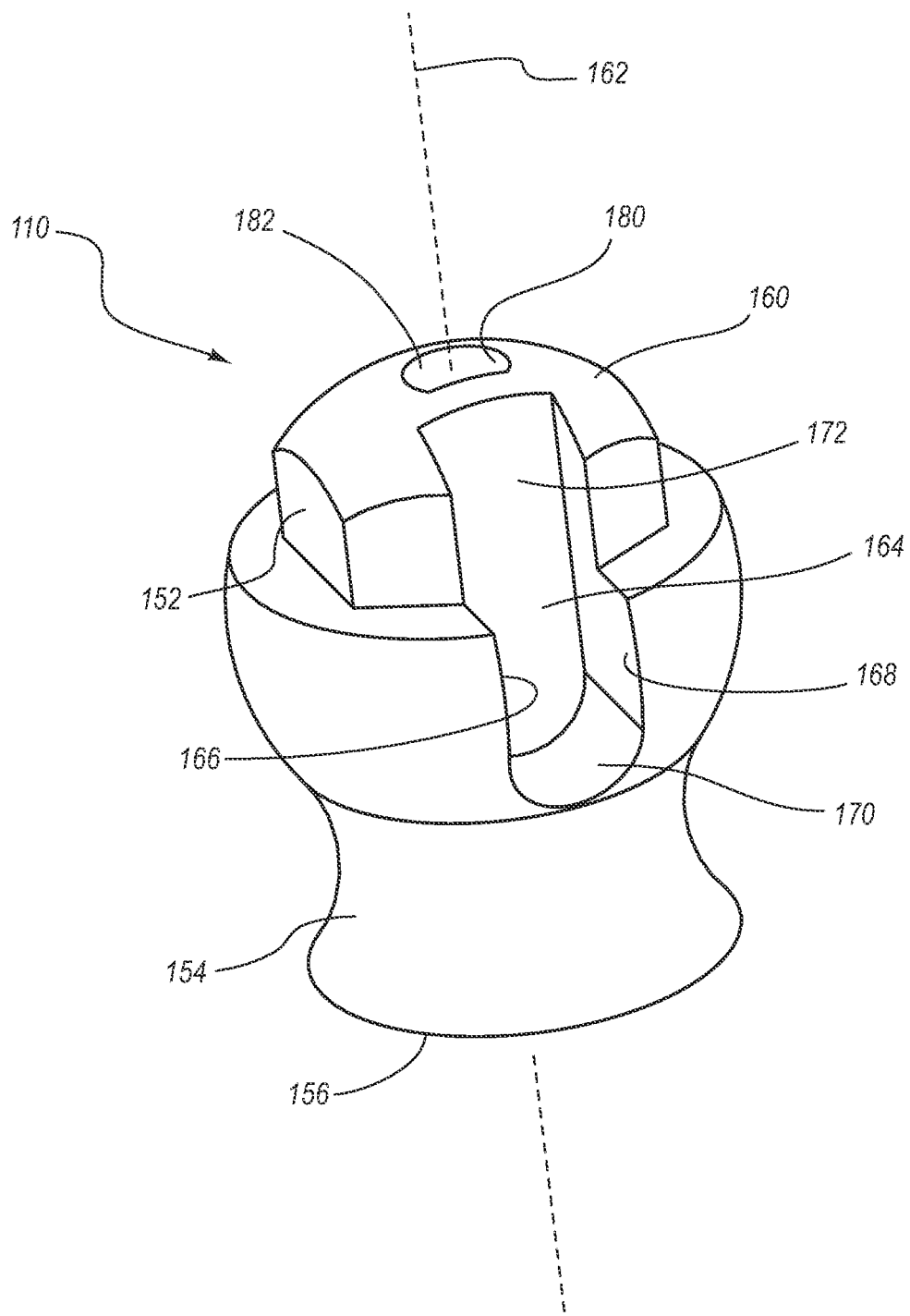
FIG. 5 is a top perspective view of the head portion of the bone screw shown in FIG. 2.

Turning to FIG. 5, head 110 includes a central longitudinal axis 162 extending through head 110 between top surface 160 of top portion 152 and bottom surface 156 of neck 154. When bone screw 102 is assembled, axis 118 of shaft 108 (see FIG. 4) and axis 162 of head 110 are aligned with each other.

An engagement slot 164 is formed on head 110. Engagement slot 164 comprises a pair of opposing side walls 166 and 168 that are generally disposed in parallel planes and extend to a rounded floor 170 and a back wall 172. Back wall 172 typically intersects with floor 170 at a right angle while back wall 172 is disposed generally parallel to central longitudinal axis 162 at a distance spaced apart therefrom. In alternative embodiments, floor 170 need not be rounded but can be flat, V-shaped, or have other configurations. It is appreciated that engagement slot 164 can have a variety of different configurations and merely needs to be sized, shaped, and oriented to permit the desired pivoting of collar 104 and rotation of bone screw 102 as will be discussed below in greater detail.

Figure 6:
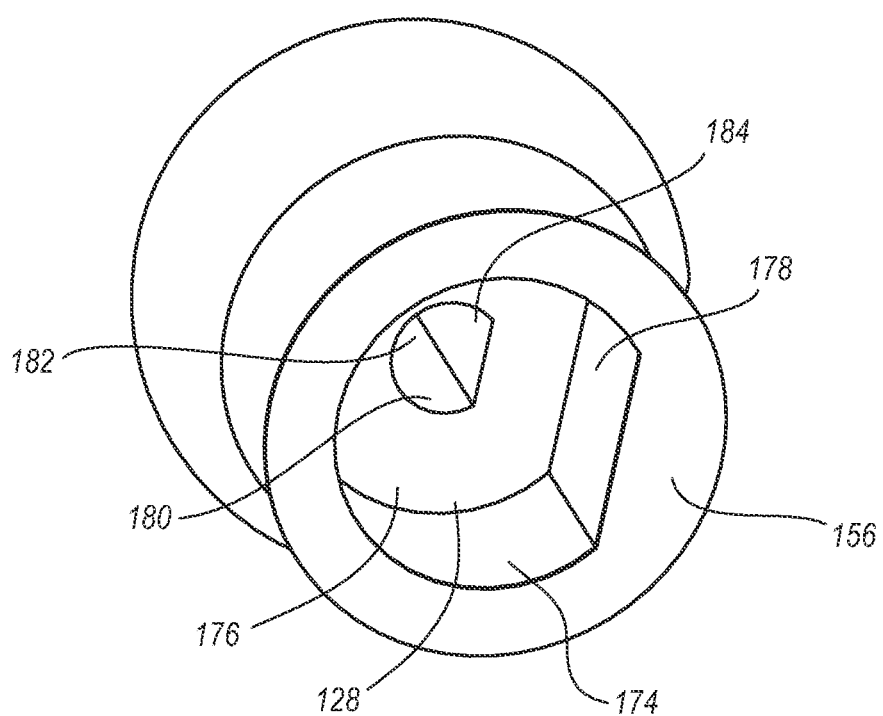
FIG. 6 is a bottom perspective view of the head portion of the bone screw shown in FIG. 2.

Turning to FIG. 6, attachment recess 128 is formed in bottom surface 156 of head 110 to mate with attachment member 126 of shaft 108 (FIG. 4). As such, attachment recess 128 is sized and shaped so as to receive attachment member 126. For example, in the depicted embodiment, attachment recess 128 is bounded by an encircling side wall 174 that extends from bottom surface 156 to a floor 176. Attachment recess 128 has a straight section 178 of side wall 174 corresponding to flat 136 of side wall 130 of attachment member 126. In an alternative embodiment, attachment member 126 is disposed on head 110 and attachment recess 128 is formed on shaft 108. It is appreciated that attachment member 126 and attachment recess 128 can have a variety of different configurations and merely need to be sized, shaped, and oriented to permit attachment member 126 and attachment recess 128 to selectively mate with each other when head 110 and shaft 108 are secured together, as will be discussed below in greater detail.

Returning to FIG. 5 in conjunction with FIG. 6, similar to shaft 108, head 110 includes an internal surface 180 bounding a second passageway 182 that extends through head 110. Second passageway 182 extends along central longitudinal axis 162, between top surface 160 and attachment recess 128 (or attachment member 126, if attachment member 126 is disposed on head 110). Second passageway 182 can be of the same cross-sectional shape as first passageway 140 or can be of a different shape. For example, in the depicted embodiment, second passageway 182 has a substantially circular cross sectional shape except for a straight portion 184 on one of the sides. Other shapes are also possible.

Head 110 can comprise a radiolucent material and/or a radiopaque material. In one embodiment, head 110 comprises a radiopaque metal, such as titanium, stainless steel, tungsten, alloys, or other biocompatible metals. In one embodiment, head 110 comprises the same radiolucent material as shaft 113.

Returning to FIG. 2, core 112 comprises a slender rod that extends between a proximal end 200 and an opposing distal end 202. Core 112 is designed to fit within first and second passageways 140 and 182 of assembled shaft 108 and head 110, respectively.

Figure 7:
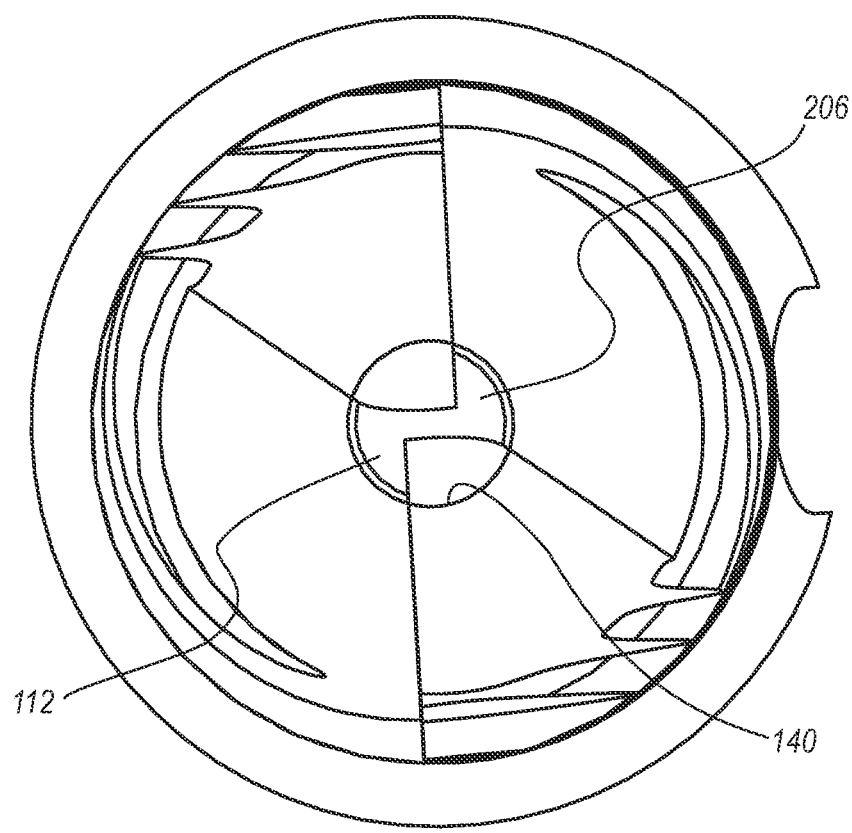
FIG. 7 is a bottom plan view of the assembled bone screw shown in FIG. 3.

Core 112 comprises a head portion 204 at proximal end 200 and a shaft portion 206 at distal end 202. Head portion 204 of core 112 is shaped to fit within second passageway 182 of head 110 and shaft portion 206 is shaped to fit within first passageway 140 of shaft 108. For example, in the embodiment depicted, shaft portion 206 has a substantially circular cross section (see FIG. 7) to fit within the circularly shaped first passageway 140, and head portion 204 has a substantially circular cross section with a segment removed to form a straight section 208 so as to match the shape of second passageway 182. In some embodiments, the cross-sectional shapes of head portion 204 and shaft portion 206 comprise the same shape.

Figure 8A:
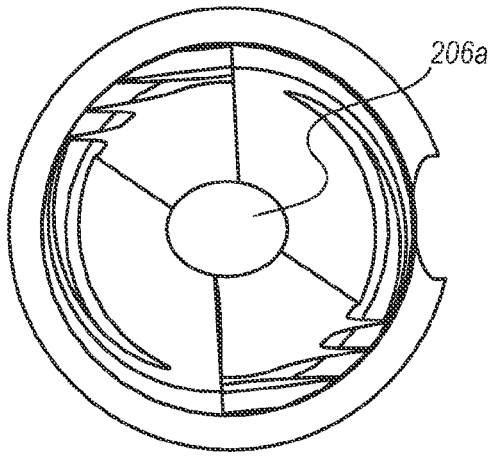
FIGS. 8A-8D are cross-sectional bottom views of alternative embodiments of bone screws.
Figure 8B:
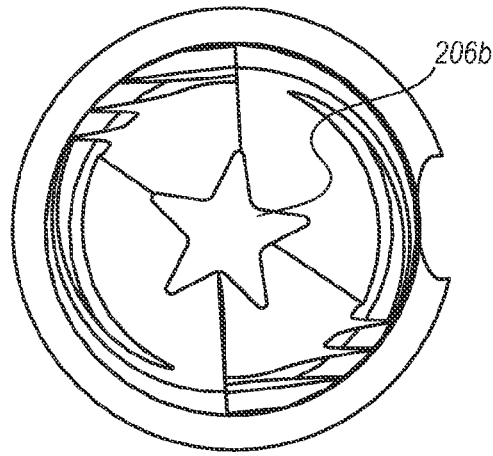
Figure 8C:
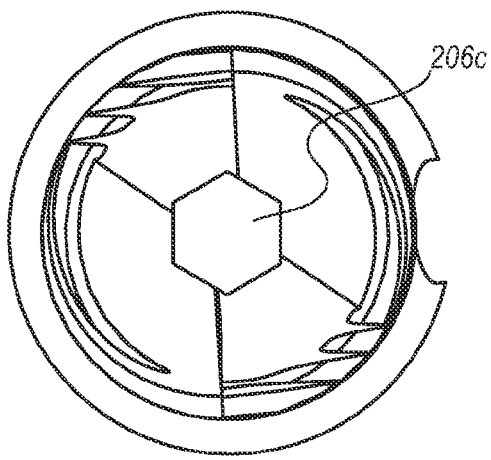
Figure 8D:
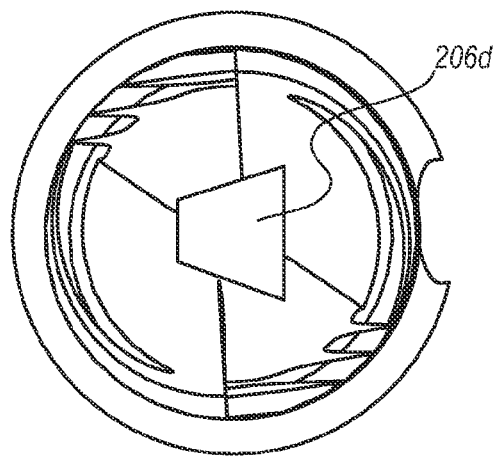

Various geometric cross sectional shapes can alternatively be used for the head portion 204 and/or the shaft portion 206 of core 112. For example, FIGS. 8A-8D disclose various embodiments of shaft portion 206 having different cross sectional shapes. FIG. 8A shows an embodiment in which shaft portion 206a is oval shaped. FIG. 8B shows an embodiment in which shaft portion 206b is generally star shaped. FIG. 8C shows an embodiment in which shaft portion 206c is generally polygonal shaped. In some embodiments head portion 204 and/or shaft portion 206 have a symmetrical cross sectional shape, such as shaft portion 206c shown in FIG. 8C; in other embodiments head portion 204 and/or shaft portion 206 have a non-symmetrical cross sectional shape, such as shaft portion 206d shown in FIG. 8D. Head portion 204 and/or shaft portion 206 can also use a combination of curved and linear segments, such as head portion 204 shown in FIG. 2. It is appreciated that the aforementioned core shapes are exemplary only and that other shapes can alternatively be used. It is appreciated that the passageways in bone screw 102 in which core 112 is received can have the same complementary configuration as core 112. One benefit of producing core 112 with a non-circular configuration is that greater engagement can be formed between core 112 and bone screw 102, thereby minimizing the potential for separation therebetween.

In one embodiment, core 112 has a maximum diameter that is less than about 3 millimeters and more commonly less than about 2 millimeters. Other diameters or widths can also be used.

Core 112 is typically comprised of a radiopaque material. Examples of such materials that can be used in core 112 are titanium, stainless steel, tungsten, alloys, or other biocompatible metals. In some embodiments, core 112 is comprised of the same material as head 110. One advantage of using a radiopaque material in core 112 while using a radiolucent material in shaft 108 is that only the thin core 112 will be seen on an X-ray during and after implantation of bone screw 102. This aids the surgeon in positioning bone screw 102 when implanting bone screw 102, yet allows other internal body structures to be viewed by X-ray during and after bone screw 102 implantation. In an alternative embodiment, however, core 112 can be comprised of a radiolucent material, such as those previously discussed with regard to shaft 108.

Figure 9:
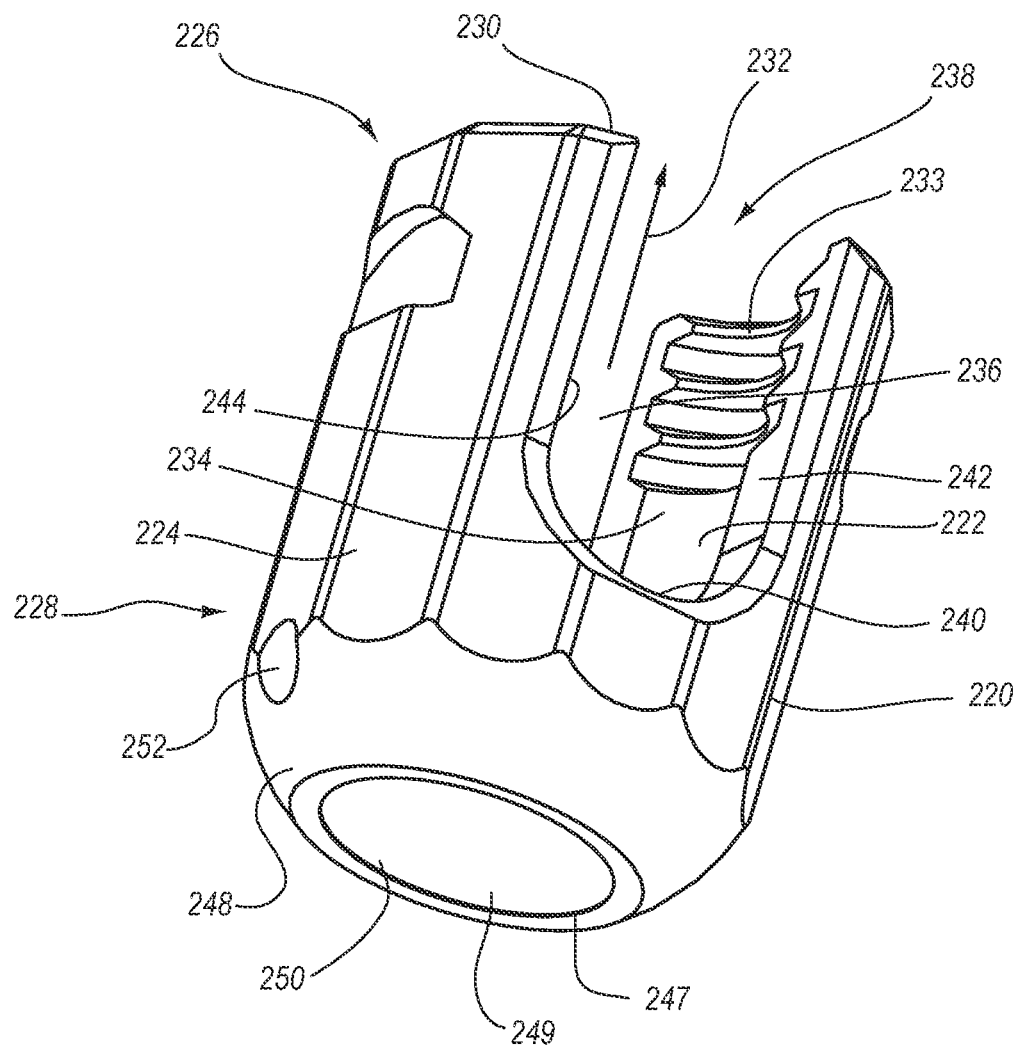
FIG. 9 is a perspective view of the collar shown in FIG. 2.

Turning to FIG. 9, collar 104 comprises a tubular side wall 220 having an interior surface 222 and an exterior surface 224 that each extend between a first end 226 and an opposing second end 228. First end 226 terminates at a terminal end face 230. Interior surface 222 bounds a longitudinal passage 232 that longitudinally extends through collar 104. Internal threads 233 are formed on interior surface 222 at or toward first end 226.

Side wall 220 is formed having a pair of channels 234 and 236 that are disposed on opposing sides of side wall 220 and that transversely extend through side wall 220. In the embodiment depicted, channels 234 and 236 each have a substantially U-shaped configuration. Each channel 234 and 236 has an open mouth 238 that extends through end face 230 and an opposing floor 240 that is rounded. Each channel 234 and 236 is configured so that stabilizing rod 107 (FIG. 1) can be received therein. In alternative embodiments, floor 240 need not be rounded but can be flat, V-shaped, or have other configurations. Each of channels 234 and 236 is also bounded by opposing side surfaces 242 and 244. Although side surfaces 242 and 244 are shown as being in substantially parallel alignment, in alternative embodiments side surfaces 242 and 244 can be designed to diverge or converge as they project away from floor 240. Other configurations can also be used. Channels 234 and 236 form a portion of a transverse passage that transversely extends through collar 104, as identified by arrow 246 (see FIG. 1).

As shown in FIG. 9, collar 104 further comprises a shoulder 248 that downwardly and radially inwardly projects from second end 228 of side wall 220. Shoulder 248 terminates at an inside edge 247 that bounds an opening 249. Opening 249 forms part of a longitudinal passage that also extends through collar 104, as identified by arrow 232, and that orthogonally intersect with transverse passage 246 (FIG. 1).

Figure 14:
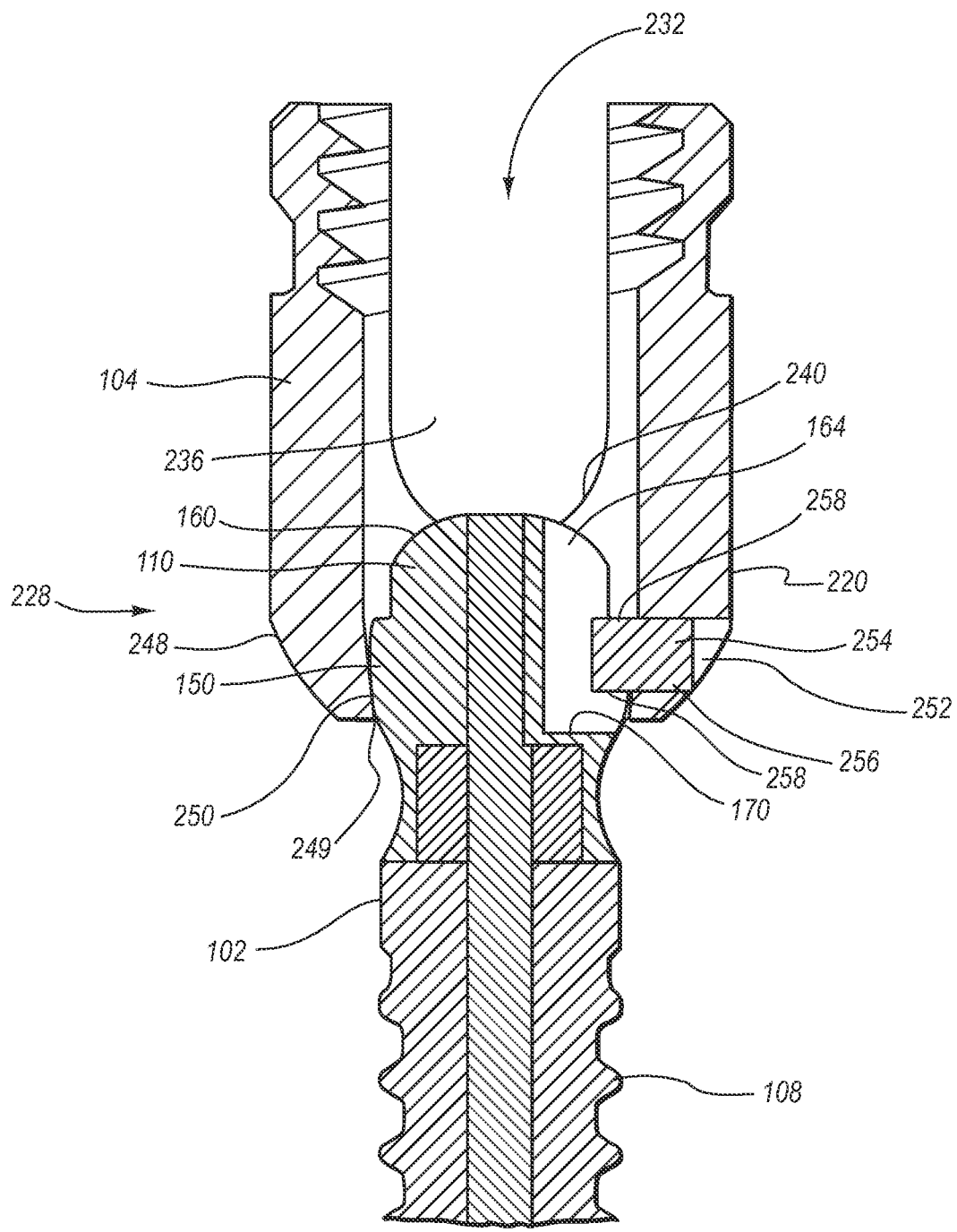
FIG. 14 is a cross sectional side view of a portion of the assembled polyaxial screw shown in FIG. 1.

Shoulder 248 has a tapered interior surface that forms an annular seat 250. As will be discussed below in greater detail, bottom portion 150 of head 110 of bone screw 102 (FIG. 3) rests against seat 250 so that collar 104 can pivot relative to bone screw 102. In this regard, as depicted in FIG. 14, bottom portion 150 of head 110 has a maximum diameter larger than opening 249 of collar 104 so that head 110 cannot pass therethrough. It is also noted that when head 110 is received within opening 249, top surface 160 of head 110 projects slightly above floor 240 of channels 234 and 236 of collar 104. As a result, as will be discussed further below, when stabilizing rod 170 (FIG. 1) is received within channels 234 and 236, stabilizing rod 170 biases against top surface 160 of head 110 so as to wedge head 110 within opening 249 and thereby lock bone screw 102 relative to collar 104.

As also depicted in FIG. 14, a pin hole 252 transversely extends through side wall 220 and/or shoulder 248 at second end 228 of side wall 220. Although not required, pin hole 252 is typically disposed orthogonal to transverse passage 246. As will also be discussed below in greater detail, pin hole 252 is adapted to receive a pin 254 which has a first end 256 and an opposing second end 258. Collar 104 and pin 254 are typically comprised of a radiopaque material such as titanium, stainless steel, tungsten, alloys, or other biocompatible metals. In alternative embodiments, however, collar 104 and/or pin 254 can be comprised of a radiolucent material, such as those previously discussed with regard to shaft 108.

Returning to FIG. 1, fastener 106 comprises a locking screw 270 having an encircling side wall 272 that extends between a top end face 274 and an opposing bottom end face 276. Optionally, movably attached to bottom end face 276 of locking screw 270 is an alignment cap 278 having a substantially U-shaped channel 280 extending transversally therethrough. Channel 280 is bounded by two side surfaces 286 and 288. Alignment cap 278 is rotatably attached to locking screw 270 so that as locking screw 270 is rotated, alignment cap 278 can remain rotationally stationary so as to bias against rod 107.

Radially outwardly projecting from side wall 272 of locking screw 270 so as to encircle locking screw 270 is a helical thread 282. Recessed on top surface 274 is a polygonal socket 284 adapted to receive a driver. Threads 282 of locking screw 270 are configured to threadedly engage with internal threads 233 of collar 104 (FIG. 9). Accordingly, once stabilizing rod 107 is disposed within transverse passage 246 of collar 104, locking screw 270 can be screwed into longitudinal passage 232 of collar 104 so that fastener 106 biases stabilizing rod 107 against head 110 of bone screw 102. If alignment cap 278 is used, surfaces 286 and 288 of the U-shaped channel 280 bias against stabilizing rod 107; otherwise bottom end face 276 of locking screw 270 biases against stabilizing rod 107. In this configuration, stabilizing rod 107 is secured from unwanted movement by being compressed between fastener 106 and head 110 of bone screw 102 and/or between fastener 106 and floor 240 of channels 234 and 236. Furthermore, as stabilizing rod 107 pushes against head 110, head 110 is wedged against seat 250 of collar 104, thereby also locking collar 104 relative to bone screw 102.

Collar 104 and fastener 106 are simply one example of a collar and fastener that can be used with bone screw 102 described herein. Other collars and associated fasteners can alternatively be used, such as the collars and fasteners described in U.S. patent application Ser. No. 11/863,133, filed Sep. 27, 2007, which is incorporated herein by specific reference.

Methods of manufacturing and assembling the bone screw 102 and polyaxial screw 100 will now be discussed.

To manufacture bone screw 102, core 112 is formed from a radiopaque or radiolucent biocompatible material, such as titanium, stainless steel, tungsten, alloy, or other material. Core 112 can be formed by any conventional method known in the art.

Figures 10, 11:
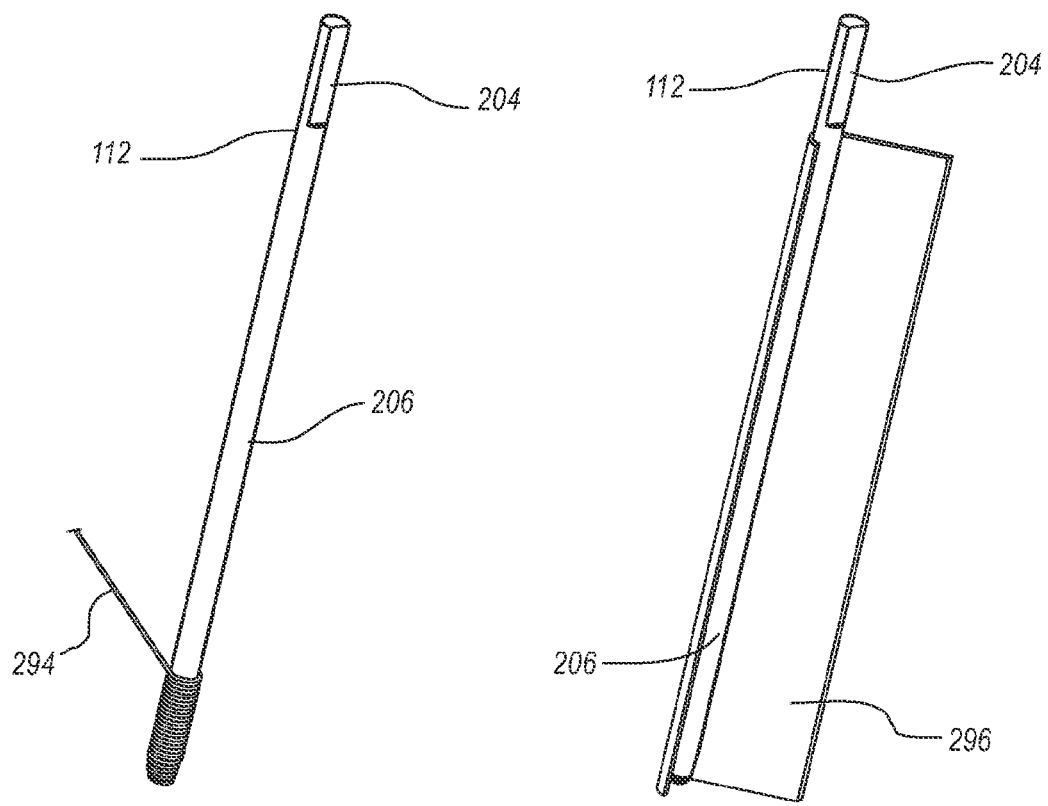
FIG. 10 is a perspective view of impregnated fibers being wound on the core shown in FIG. 2.
FIG. 11 is a perspective view of sheets of fibers being wound on the core shown in FIG. 2.
Figure 12:
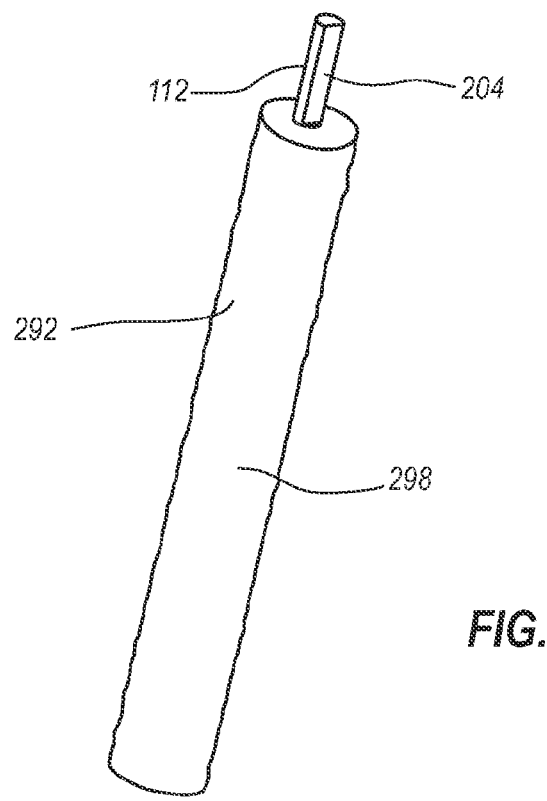
FIG. 12 is a perspective view of a blank that is formed during manufacture of the bone screw shown in FIG. 3 according to one embodiment.

Shaft 108 is then formed about shaft portion 206 of core 112 to produce a blank 292, as shown in FIGS. 10-12. Blank 292 can be formed in a number of ways. In some embodiments, blank 292 can be formed by winding fiber impregnated with epoxy resin, molten plastic or other adhesive about core 112 to produce a fiber and adhesive matrix. For example, in the embodiment depicted in FIG. 10, a filament winding process is used as is known in the art. In this process, filaments or fibers 294 are wound under tension over the shaft portion 206 of core 112. Core 112 rotates while a carriage (not shown) moves back and forth along the longitudinal direction of core 112, laying down fibers 294 in a desired pattern. Fibers 294 are coated with the epoxy resin, molten plastic or other type of adhesive as the fibers 294 are wound about core 112. If positioning ring 147 is used, it is positioned in its desired location during the filament winding process so that positioning ring 147 becomes enveloped by the outer layers of fibers 294. The winding process continues until the diameter of the blank 292 is greater than the desired diameter of the finished shaft 108 of bone screw 102. Blank 292 is then allowed to cure or harden. If required, blank 292 can be placed in an oven during the curing process.

In an alternative embodiment, blank 292 is formed using a roll wrap or table wrap process, as depicted in FIG. 11. In this process, one or more sheets 296 of fiber are impregnated with the epoxy resin, molten plastic, or other type of adhesive. If required, the impregnated sheet or sheets 296 are then allowed to partially cure. Once the desired amount of partial curing has been obtained, the sheet or sheets 296 are then wrapped about the shaft portion 206 of core 112 to produce a fiber and adhesive matrix. If positioning ring 147 is used, it is positioned in its desired location during the wrapping process so that positioning ring 147 becomes enveloped by the outer layers of sheets 296. The wrapping continues until the diameter of the blank 292 is greater than the desired diameter of the finished shaft 108 of bone screw 102. Blank 292 is then allowed to cure in a similar manner to the filament winding process, described previously.

It is also appreciated that non-winding methods can also be used for forming blank 292 about core 112. For example, compression molding or other conventional molding processes can be used to mold a fiber/adhesive mixture about core 112. In this embodiment, the fibers can be short fiber pieces that are distributed throughout the adhesive. Other known methods can alternatively be used to form blank 292.

As the impregnated fibers 294 or sheets 296 are only wound around shaft portion 206 of core 112, the head portion 204 of core 112 remains open and uncovered, as shown in FIG. 12. To allow for a better bond between core 112 and the wound fiber and adhesive matrix, the surface of core 112 can be etched or otherwise abraded before the fibers 294 or sheets 296 are wound thereon. This can be accomplished by sand blasting, rubbing with sandpaper, chemical etching, or other known roughening process, if desired.

Once the blank 292 has been formed and allowed to cure, a grinder can be used, if desired, to smooth out any sharp edges remaining on the exterior surface 298 of the blank 292. Attachment member 126 and helical threads 120 (see FIG. 4) are then formed on the exterior surface 298 of the blank 292 to further form shaft 108. This can be accomplished by removing a portion of the exterior surface 298 of the blank 292 by using a grinder, lathe, or other cutting tool as is known in the art. Other methods of forming attachment member 126 and threads 120 can alternatively be used.

Tapered tip 124 (see FIG. 4) can also be formed at the distal end of the shaft 108, if desired. In one embodiment, tapered tip 124 is formed by removing a portion of the exterior surface 298 of the blank 292. Any other features, such as those needed for self tapping, can also be formed if desired.

Figure 13:
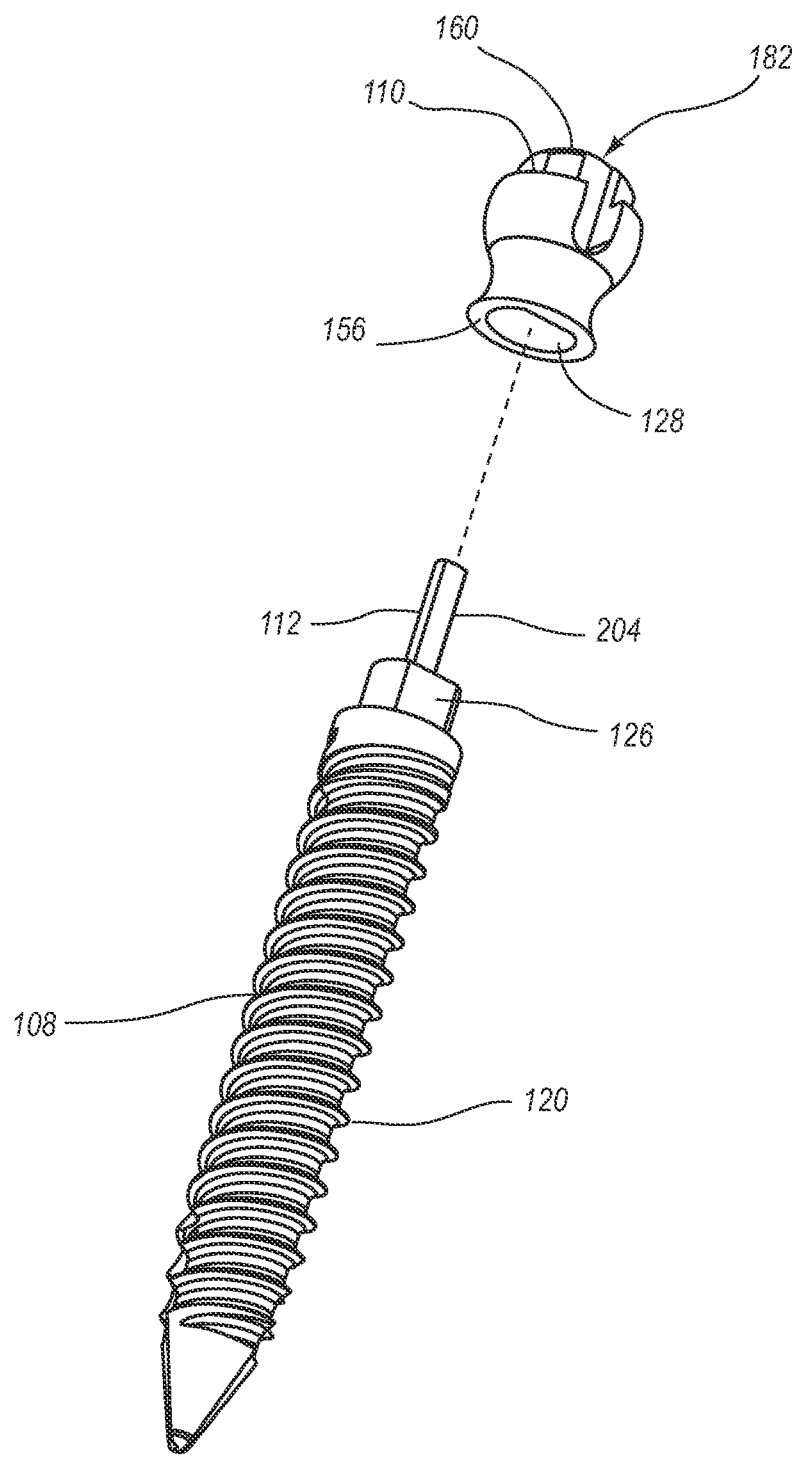
FIG. 13 is a perspective view of a portion of the polyaxial screw shown in FIG. 3 in a partially assembled state.

Turning to FIG. 13, once attachment member 126 and threads 120 have been formed on the shaft 108, head 110, which has been previously formed, is then attached to the threaded shaft 108. To do this, bottom surface 156 of head 110 is positioned adjacent head portion 204 of core 112 so that second passageway 182 aligns with core 112. Head 110 is then advanced toward shaft 108 so that head portion 204 of core 112 is received within second passageway 182. Head 110 is further advanced along core 112 until attachment member 126 is received within attachment recess 128. Head 110 is rigidly secured to core 112 and to shaft 108 by adhesive, laser welding, and/or other securing method known in the art. For example, in addition to using an adhesive between head 110 and shaft 108 and between head 110 and core 112, if desired, the exposed end of core 112 can be directly welded to head 110. Any portion of core 112 that extends out of second passageway 182 and past top surface 160 of head 110 can be cut off, if desired.

If ring layer 148 is used, it is positioned or painted on or within threads 120 after threads 120 have been formed on exterior surface 122 of shaft 108, as depicted in FIG. 16. This can occur anytime after threads 122 have been formed, including before or after head 110 is attached and secured to shaft 108.

Figure 13A:
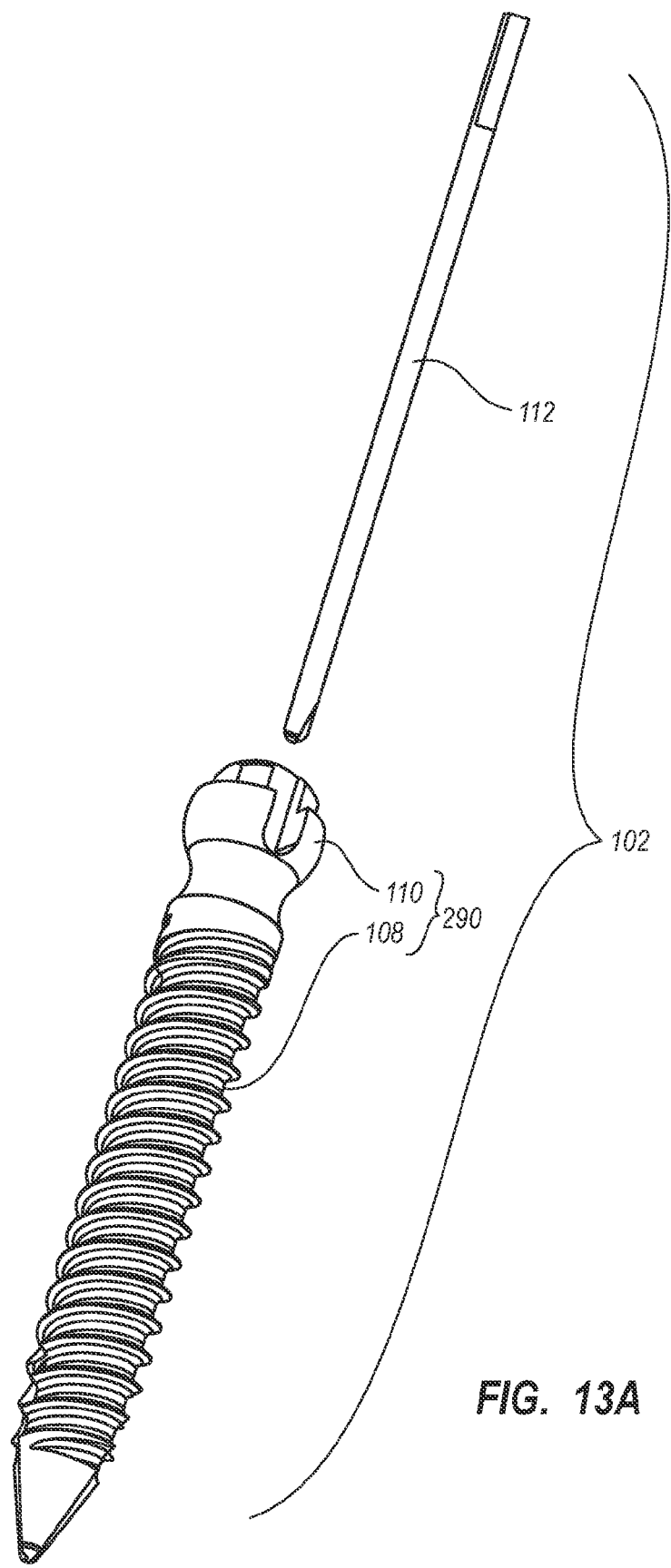
FIG. 13A is an exploded perspective view of an alternative embodiment of the bone screw shown in FIG. 13 wherein the head and the shaft of the bone screw are integrally formed as a unitary member.

In an alternative method of manufacturing bone screw 102, after core 112 has been formed, blank 292 is configured so that both head portion 204 and shaft portion 206 can be formed therefrom. Specifically, depicted in FIG. 13A, bone screw 102 is shown as being comprised of a body 290 and core 112 that is positioned therein. Body 290 comprises shaft 108 and head 110. However, in contrast to the prior embodiment where head 110 is secured to shaft 108, in this embodiment shaft 108 and head 110 are integrally formed as a single unitary structure. That is, both shaft 108 and head 110 are milled, cut or otherwise formed from a single blank that is formed about core 112. As such, in this embodiment the entire body 290 is comprised of a radiolucent material, such as those previously discussed with regard to shaft 108, while core 112 is typically comprised of a radiopaque material but can also be comprised of a radiolucent material. As with other embodiments, positioning ring 147 (FIG. 15) and ring layer 148 (FIG. 16) can also be used with body 290.

In one similar method of manufacture, body 290 can initially be formed by winding a radiolucent fiber/adhesive matrix about a core 112 that is formed from a high strength radiopaque material, such as a metal. In contrast to prior embodiments, however, core 112 is then slid out of body 290. The remaining passageway can then be backfilled by injecting a radiolucent material such as an epoxy or other adhesive within the passageway. Alternatively, a radiolucent core can be slid into the passageway and secured in place by an adhesive or other method of securing. As a result, the entire body and core are radiolucent. To help facilitate placement, positioning ring 147 (FIG. 15) and/or ring layer 148 (FIG. 16) can be used with the radiolucent body.

Once bone screw 102 has been manufactured and assembled as described above, the polyaxial screw 100 can be assembled with bone screw 102 as one of its components. For example, turning to FIG. 14, to assemble polyaxial screw 100, shaft 108 of assembled bone screw 102 is passed down through longitudinal passage 232 and opening 249 of collar 104. Head 110 of bone screw 102, however, has a maximum diameter that is greater than the minimum diameter of opening 249 extending through seat 250 of collar 104. As such, head 110 of bone screw 102 rests on seat 250 of collar 104 and is prevented from passing through opening 249. As a result of the rounded configuration of bottom portion 150 of head 110 and the tapered sloping of seat 150, head 110 can freely slide on seat 250 such that bone screw 102 and collar 104 can freely pivot relative to each other.

Once bone screw 102 is seated within collar 104, pin 254 is advanced into pin hole 252. First end 256 of pin 254 is secured within pin hole 252 such as by welding, adhesive, press fit, or other mechanical engagements, such as threaded engagement. In this positions second end 258 of pin 254 projects into engagement slot 164 of bone screw 102. It is noted that pin 254 is spaced apart above floor 170 of engagement slot 164. As a result, bone screw 102 and collar 104 can continue to freely pivot relative to each other. However, because pin 254 extends over floor 170, head 110 is prevented from passing back up through collar 104. Pin 254 also functions to couple bone screw 102 and collar 104 together so that rotation of collar 104 or bone screw 102 also facilitates rotation of the other of the collar 104 or bone screw 102. As such, bone screw 102 can be implanted or removed simply by rotating collar 104. In alternative embodiments, it is appreciated that pin 62 can come in a variety of different configurations and can be mounted at a variety of different orientations and locations. Pin 62 can also be comprised of a radiolucent or radiopaque material.

In an alternative embodiment, head 110 is mounted on the collar 104 using pin 254, as described above, before head 110 is attached and secured to core 112 and shaft 108.

Figure 17:
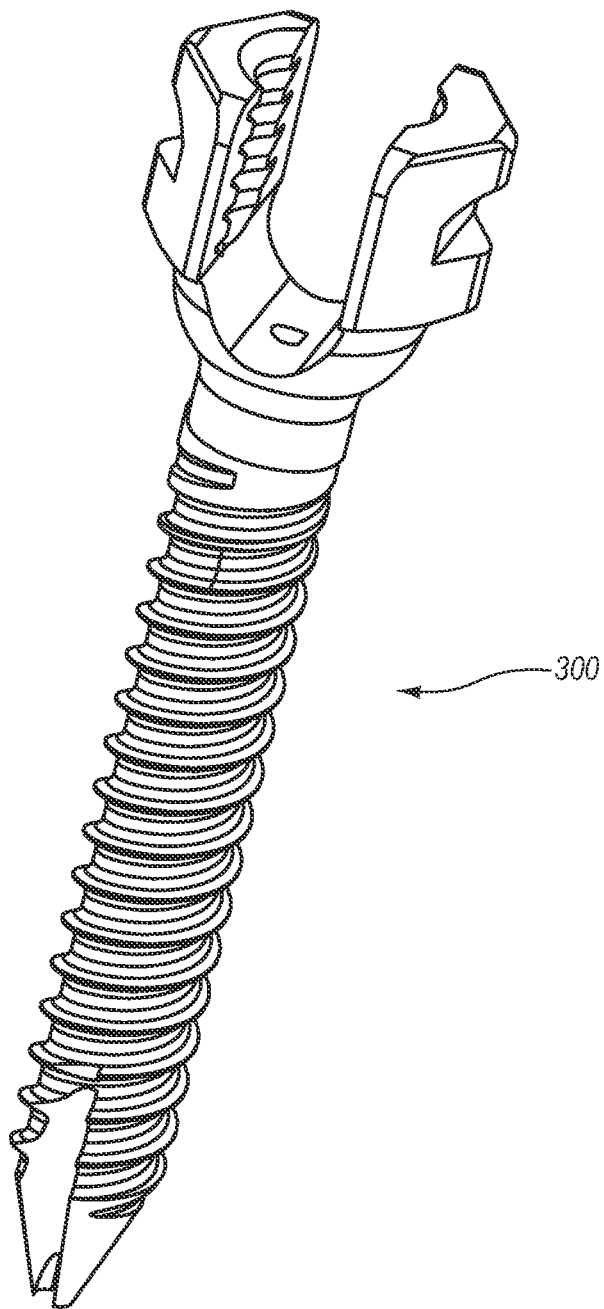
FIG. 17 is one embodiment of a fixed bone screw wherein a collar is rigidly secured to the end of the shaft.

Depicted in FIG. 17 is one embodiment of a fixed bone screw 300 incorporating features of the present invention. In general, fixed bone screw 300 comprises a collar rigidly secured to or formed on the end of a threaded shaft so that the collar cannot pivot relative to the shaft. Like elements between bone screw 300 and the prior discussed embodiments are identified by like reference characters.

Figure 18:
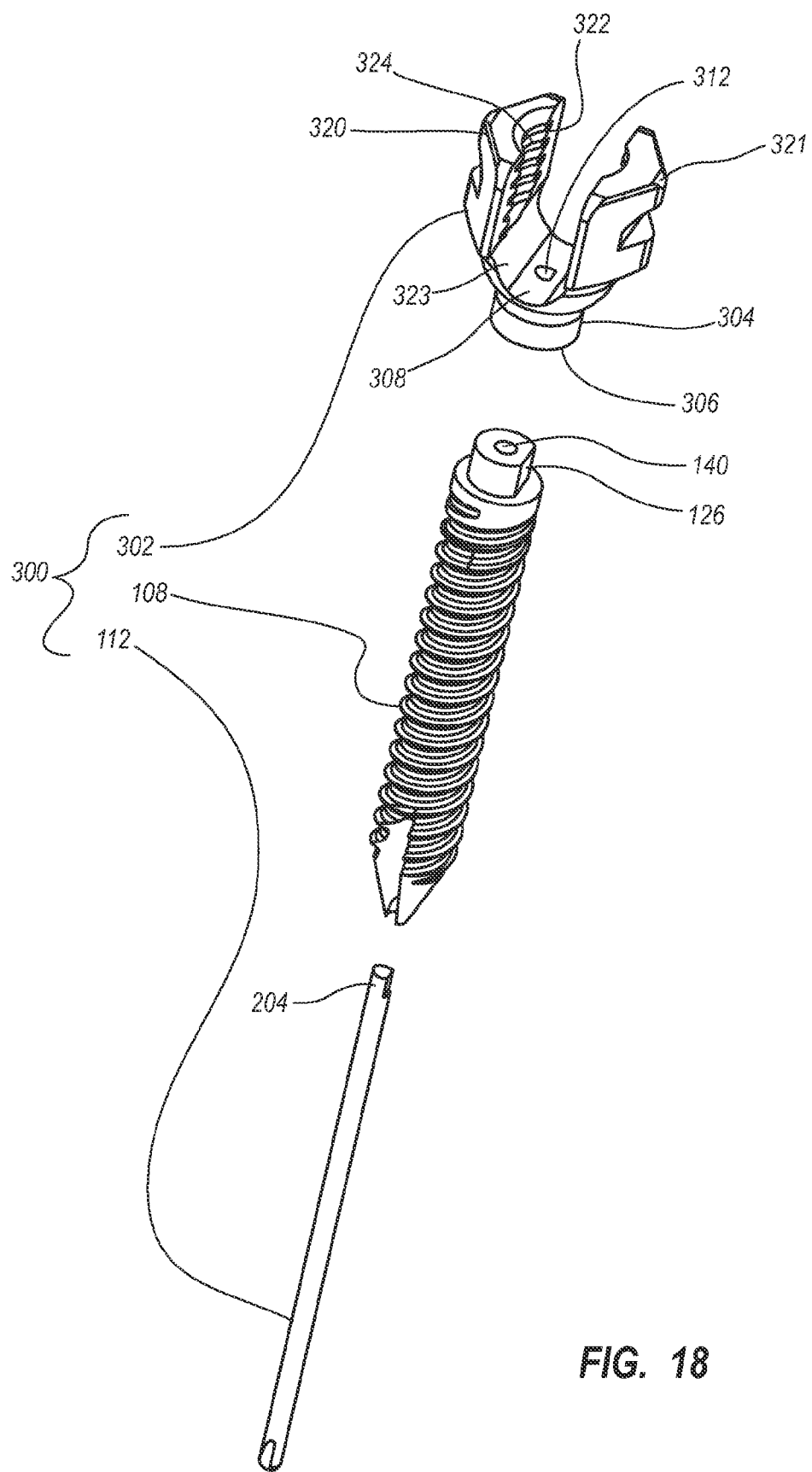
FIG. 18 is an exploded view of the bone screw shown in FIG. 17.

As depicted in FIG. 18, in one embodiment bone screw 300 comprises shaft 108, core 112, and a collar 302. Core 112 is secured within first passageway 140 of shaft 108. The previously discussed materials, configurations, methods of manufacture and alternatives thereof of shaft 109 and core 112 are also applicable to bone screw 300.

Figure 19:
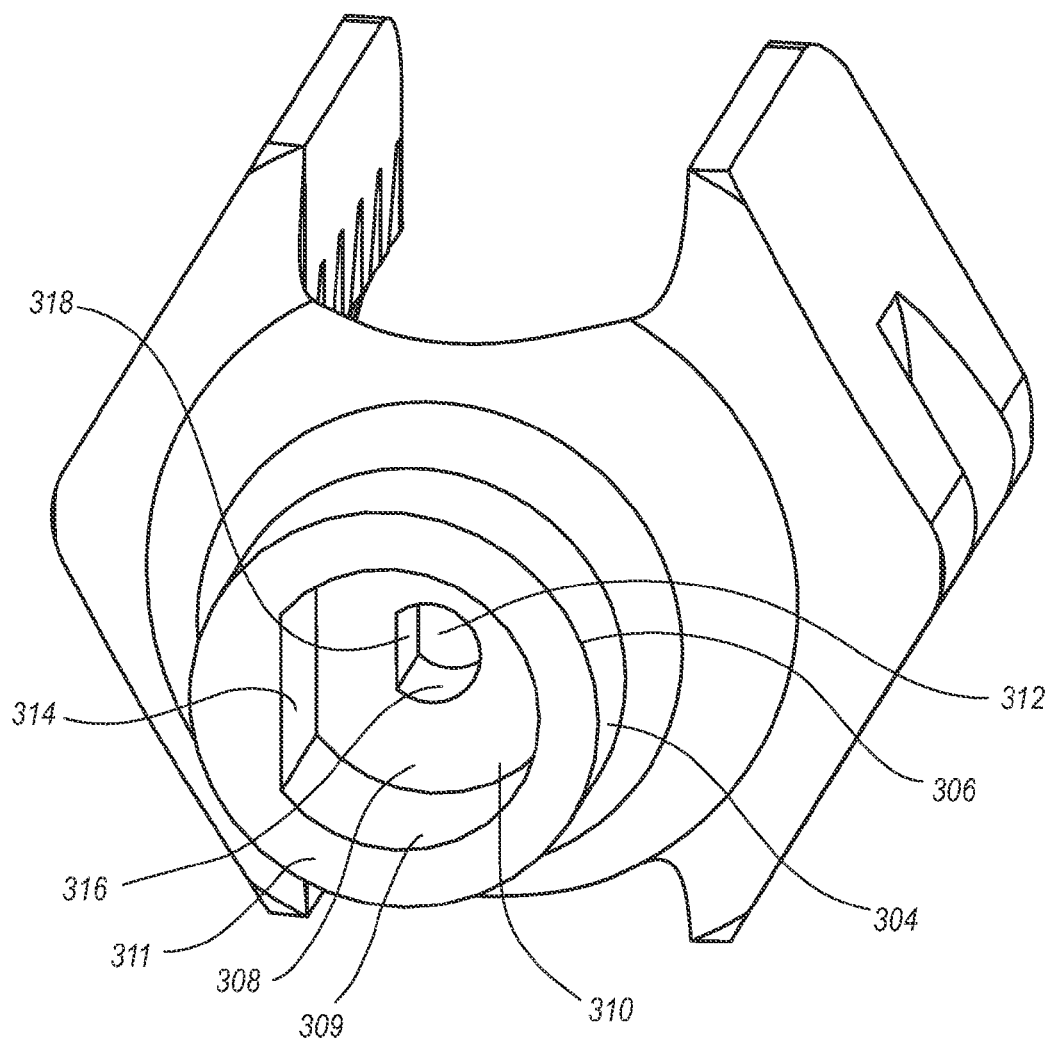
FIG. 19 is a perspective bottom view of the collar shown in FIG. 18.

As depicted in FIGS. 18 and 19, collar 302 comprises a base 304 that extends from a first end 306 to a floor 308. Base 304 has an interior surface 309 that bounds an attachment recess 310 extending from floor 308 to a first end face 311 at first end 306. Attachment recess 310 thus has the configuration of a blind socket. Interior surface 309 has a substantially circular transverse cross section with a flat 314 formed thereon. Attachment recess 310 has a configuration complimentarily to and is configured to receive and secure to attachment member 126 of shaft 108 in the same manner that attachment member 126 is received and secured within attachment recess 128 of head 110 (FIG. 6).

Floor 308 also has an interior surface 316 that bounds a second passageway 312 that extends through floor 308 so as to communicate with attachment recess 310. Interior surface 316 also has a substantially circularly transverse cross section with a flat 318 formed thereon.

Second passageway 312 is positioned so that when attachment member 126 is secured within attachment recess 310, first passageway 140 of shaft 108 is aligned with second passageway 312. It is also appreciated that second passageway 312 is also configured to receive and secure to head portion 204 of core 112 in the same way that head portion 204 is received and secured within second passageway 182 of head 110 (FIG. 6).

A pair of spaced apart arms 320 and 321 project from opposing sides of base 304 in substantially parallel alignment. Each arm 320 and 321 has an interior surface 322. The opposing interior surfaces bound a substantially U-shaped channel 323 in which stabilizing rod 107 (FIG. 1) can be received. Furthermore, each interior surface 322 has a thread portion 324 formed thereon. Thread portions 324 enable locking screw 270 (FIG. 1) or an alternative embodiment thereof to threadedly engage with arms 320 and 321 so as to secure stabilizing rod 107 within channel 323. It is appreciated that many of the alternative design features as previously discussed with regard to collar 104 are also applicable to collar 302. Likewise, collar 302 can be comprised of the same materials as previously discussed with regard to collar 104.

To aid in the implantation of bone screw 300, positioning ring 147 (FIG. 15) and ring layer 148 (FIG. 16), as previously discussed, can again be formed on or within shaft 108. Likewise, as with bone screw 102, by forming shaft 108 out of a radiolucent material while core 112 and collar 302 are formed from a radiopaque material, bone screw 300 can be properly positioned while limiting unwanted obstructions. Specifically, the thin core 112 can be easily viewed by X-ray to determine proper positioning of the bone screw but the larger shaft 108 is radiolucent so as to not obstruct surrounding structure.

Figure 20:
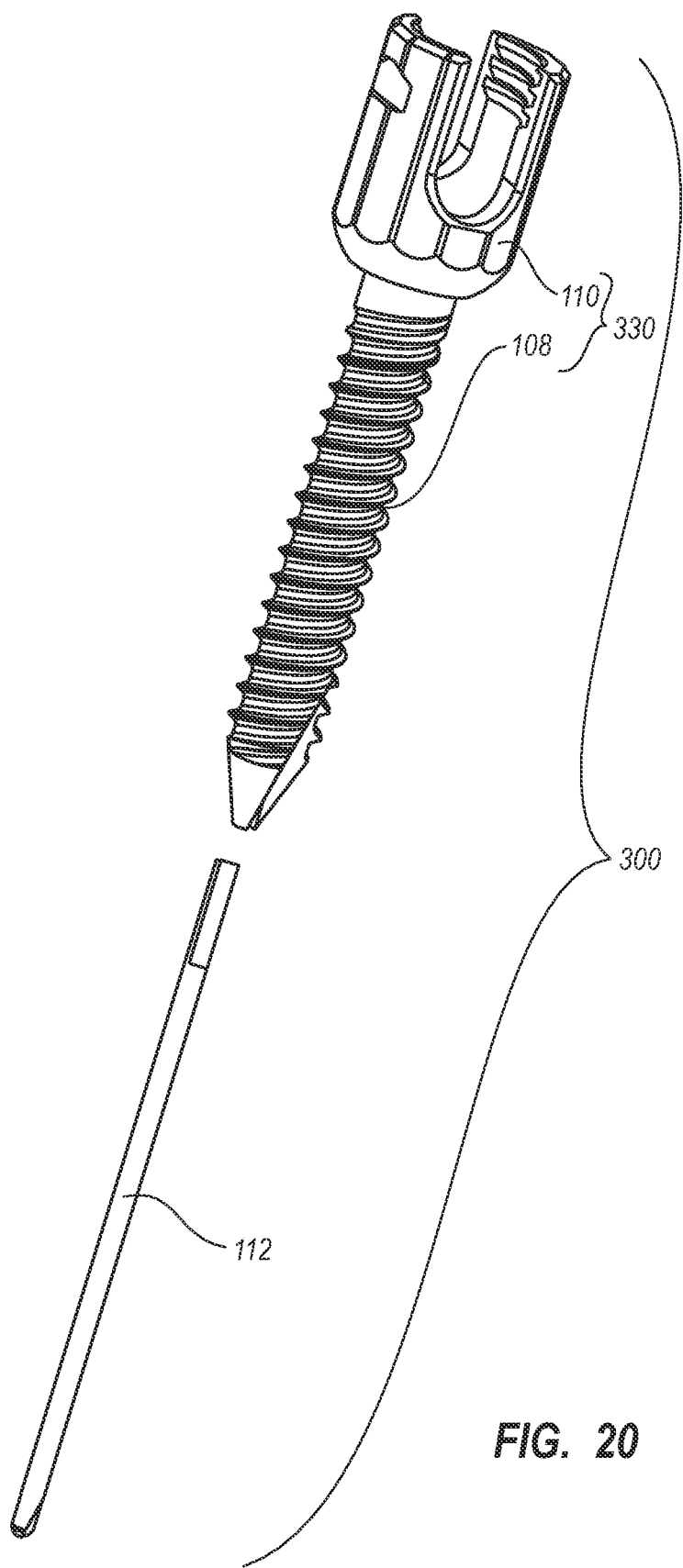
FIG. 20 is an exploded perspective view of an alternative embodiment of the fixed bone screw shown in FIG. 17 wherein the collar and the shaft of the bone screw are integrally formed as a unitary member.

Depicted in FIG. 20 is an alternative embodiment of bone screw 300. In this embodiment, bone screw 300 is shown as being comprised of a body 330 and core 112 that is positioned therein. Body 330 comprises shaft 108 and collar 302. However, in contrast to the prior embodiment where collar 302 is secured to shaft 108, in this embodiment shaft 108 and collar 302 are integrally formed as a single unitary structure. That is, both shaft 108 and collar 302 are milled, cut or otherwise formed from a single blank that is formed about core 112. As such, in this embodiment the entire body 330 is comprised of a radiolucent material, such as those previously discussed with regard to shaft 108, while core 112 is typically comprised of a radiopaque material but can also be comprised of a radiolucent material. As with other embodiments, positioning ring 147 (FIG. 15) and/or ring layer 148 (FIG. 16) can also be used with body 330. Furthermore, as discussed in prior embodiments, core 112 can be removed and replaced with an adhesive or an alternative core.

A number of different methods and embodiments are disclosed herein. It is appreciated that the different methods and components from the different embodiments can be mixed and matched to produce a variety of still other different embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a bone screw, the method comprising:
   forming an elongated shaft about a core, the shaft having a longitudinal axis extending between a proximal end and an opposing distal end, the core extending along the longitudinal axis, the shaft being comprised of a radiolucent material and the core being comprised of a radiopaque metal, the shaft being formed by winding a flat sheet comprised of radiolucent fibers impregnated with an adhesive directly on the radiopaque core so that the adhesive binds directly to the core and so that the fibers radially encircle the core; and
   forming a helical thread on an exterior surface of the shaft by removing a portion of the exterior surface of the shaft.

2. The method as recited in claim 1, further comprising positioning a radiopaque ring layer on the helical thread.

3. The method as recited in claim 1, further comprising attaching a head to the proximal end of the shaft.

4. The method as recited in claim 1, wherein the shaft is comprised of an etherketone and fiber matrix.

5. The method as recited in claim 4, wherein the etherketone comprises polyetheretherketone (PEEK).

6. The method as recited in claim 1, wherein the step of forming the helical thread is accomplished through the use of a grinder, lathe or cutting tool.

7. The method as recited in claim 1, wherein the fibers radially encircle the core in a helical pattern that extends along a length of the core.

8. A method of manufacturing a bone screw, the method comprising:
   wrapping a flat sheet comprised of a radiolucent adhesive and radiolucent fibers directly on a core so as to form a shaft where the radiolucent fibers radially encircle the core in a helical pattern that extends along a length of the core and the radiolucent adhesive binds directly to the core, the core being comprised of a radiopaque metal;
   allowing the radiolucent adhesive to set; and
   forming a helical thread on an exterior surface of the shaft by removing a portion of the exterior surface of the shaft.

9. The method as recited in claim 8, wherein the adhesive comprises an etherketone.

10. The method as recited in claim 9, wherein the etherketone comprises polyether etherketone (PEEK).

11. The method as recited in claim 8, wherein the step of removing a portion of the exterior surface of the shaft is accomplished through the use of a grinder, lathe or cutting tool.

12. The method as recited in claim 8, further comprising attaching a head to the core or the shaft.

13. The method as recited in claim 8, wherein at least a portion of the core has a non-circular transverse cross section.

* * * * *